US006425764B1

(12) United States Patent
Lamson

(10) Patent No.: US 6,425,764 B1
(45) Date of Patent: Jul. 30, 2002

(54) VIRTUAL REALITY IMMERSION THERAPY FOR TREATING PSYCHOLOGICAL, PSYCHIATRIC, MEDICAL, EDUCATIONAL AND SELF-HELP PROBLEMS

(76) Inventor: Ralph J. Lamson, P.O. Box 6891, San Rafael, CA (US) 94903-0891

( * ) Notice: Subject to any disclaimer, the term of this patent is extended or adjusted under 35 U.S.C. 154(b) by 0 days.

(21) Appl. No.: 08/989,778

(22) Filed: Dec. 12, 1997

Related U.S. Application Data

(60) Provisional application No. 60/049,212, filed on Jun. 9, 1997.

(51) Int. Cl.[7] .............................................. G09B 19/00
(52) U.S. Cl. ...................................................... 434/236
(58) Field of Search ............................... 434/236, 237, 434/238; 600/26, 27, 28, 300, 301

(56) References Cited

U.S. PATENT DOCUMENTS

| 4,273,540 A | 6/1981 | Dill | 434/262 |
|---|---|---|---|
| 4,327,712 A | 5/1982 | Frenkel | 600/248 |
| 4,573,472 A | 3/1986 | Ito | 607/96 |
| 4,709,700 A | 12/1987 | Hyrman | 607/45 |
| 4,717,343 A | 1/1988 | Densky | 434/236 |

(List continued on next page.)

OTHER PUBLICATIONS

Addison, R. (1995). Detour: brain deconstruction ahead. In: Satava, R. M., Morgan, K., Sieburg, H. B., Mattheus, R., & Christensen, J. P. Interactive technology and the new paradigm for healthcare, pp. 1–3. IOS Press, Amsterdam, Oxford, Washington, D.C.

American Psychiatric Association (1994). Diagnostic and statistical manual of mental disorders: Fourth Edition. DSM–IV. Washington, D.C.

Carlin, A. S., Hoffman, H. G., & Weghorst, S. (1997). Virtual reality and tactile augmentation in the treatment of spider phobia: a case report. Behavior Research Therapy, 35(2): 153–58.

Hodges, L. F., Rothbaum, B. O., Kooper, R., Opdyke, D., Meyer, T., North, M., de Graaff, J. J., and Williford, J. (1995). Virtual environment for treating the fear of heights. IEEE Computer 28, 7, pp. 27–34.

(List continued on next page.)

Primary Examiner—John Edmund Rovnak
(74) Attorney, Agent, or Firm—David Pressman

(57) ABSTRACT

A method of treating a psychological, psychiatric, or medical condition by choosing a psychological strategy for treating the condition, encoding electronic instructions for a virtual reality environment in such a way that the interactive virtual reality environment implements the psychological strategy, loading electronic instructions into a virtual reality technology unit (10, 22) equipped with a display (14, 40) for displaying the virtual reality environment and with a patient input device (14, 22, 32) for receiving responses to the environment from the patient, and instructing the human patient how and when to use the virtual reality technology unit to interact with the environment. The interactive environment contains instructions for a scoring procedure for quantitatively analyzing the medical condition of the patient, and/or counseling instructions or self-help instructions. The environment can be used in conjunction with a physical parameter measuring device (36) connected to the virtual reality technology unit (10). The process is comprehensive and takes place during immersion in fully interactive three-dimensional virtual reality environments utilizing computer generated graphics, images imported from photographs, and video for sensory stimulation. Immersion is achieved with goggles, a head-mounted-display, or other form of visual stimulation, such as surround projection screens or monitors or devices that permit the user to have a virtual experience. It includes the use of voice, music, and sound and other forms of physiological stimulation and feedback. Body sensors and devices such as a hand-held grip permit the user to interact with objects and navigate within the virtual environment.

31 Claims, 9 Drawing Sheets

U.S. PATENT DOCUMENTS

| | | | |
|---|---|---|---|
| 4,762,494 A | 8/1988 | Woods | 434/236 |
| 5,219,322 A | 6/1993 | Weathers | 600/27 |
| 5,280,793 A | 1/1994 | Rosenfeld | 128/732 |
| 5,403,263 A | 4/1995 | Rodgers | 600/28 |
| 5,429,140 A | 7/1995 | Burdea et al. | 128/774 |
| 5,435,324 A | 7/1995 | Brill | 128/897 |
| 5,450,855 A | 9/1995 | Rosenfeld | 127/732 |
| 5,546,943 A | 8/1996 | Gould | 128/653.1 |
| 5,577,981 A | 11/1996 | Jarvik | 482/4 |
| 5,584,695 A | 12/1996 | Walker et al. | 434/43 |
| 5,619,291 A | 4/1997 | Putnam | 351/240 |
| 5,655,909 A | 8/1997 | Kitchen | 434/44 |
| 5,807,114 A * | 9/1998 | Hodges et al. | 434/236 |
| 6,012,926 A * | 1/2000 | Hodges et al. | 434/236 |

OTHER PUBLICATIONS

Kooper, R. (1994). Virtually present: treatment of acrophobia by using virtual reality graded exposure. Master Thesis in Computer Science at the Technical University of Delft, Netherlands.

Lamson, R. (1989). The effects of a manual–guided cognitive intervention program upon substance abusers. Unpublished dissertation. University of Southern California.

Lamson, R. (1993). The effects of virtual reality immersion on anxiety disorders. Kaiser Foundation Research Institute.

Lamson, R. (1994). Virtual therapy of anxiety disorders: applications: VR in psychotherapy. CyberEdge Journal, Issue #20, vol. 4, No. 2. Sausalito, California.

Lamson, R. and Meisner, M. (1994). The effects of virtual reality immersion in the treatment of anxiety, panic, and phobia of heights. Proceedings for Virtual Reality and Persons with Disabilities, pp. 63–68. Second Annual International Conference, Center on Disabilities, California State University, Northridge.

Lamson, R. and Meisner, M. (1995). Clinical application of virtual therapy to psychiatric disorders: theory research, practice, Pre–Conference Workshop, Medicine Meets Virtual Reality #4.

Lamson, R. (1997). Virtual Therapy: prevention and treatment of psychiatric conditions in virtual reality environments. Polytechnic International Press. Montreal Canada. ISBN 2–553–00631–4.

Maier, S. F., Watkins, L. R., and Fleshner, M. (1994). Psychoneuroimmunology: the interface between brain, behavior, and immunity. American Psychologist, 49(12): 1004–17.

Mannings, T. R. (1995). The emotional dimension of experience in information environments. In: Satava, R. M., Morgan, K., Sieburg, H. B., Mattheus, R., & Christensen, J. P. Interactive technology and the new paradigm for healthcare, pp. 231–236 . IOS Press, Amsterdam, Oxford, Washington, D.C.

North, M. M., North, S. M., and Coble, J. R. (1997). Virtual reality therapy for fear of flying. Letter to the editor, American Journal of Psychiatry, 154:1, p. 130.

Pimentel, K. and Teixeira, K. (1993). Virtual Reality: through the new looking glass. Intel/Windcrest/McGraw–Hill, Inc. New York.

Rothbaum, B. O., Hodges, L. F., Kooper, R., Opdyke, D., Williford, J., and North, M. (1995a). Virtual reality graded exposure in the treatment of acrophobia: a case study. Behavior Therapy, vol. 26, No. 3, pp. 547–554.

Rothbaum, B. O., Hodges, L. F., Kooper, R., Opdyke, D., Williford, J., and North, M. (1995b). Effectiveness of computer–generated (virtual Reality) graded exposure in the treatment of acrophobia. American Journal Psychiatry, vol. 152, No. 4, pp. 626–628.

Lamson et al, "The Effects of Virtual Reality Immersion in the Treatment of Anxiety, Panic, & Phobia of Heights", Jun. 1994, Proceedings: Virtual Reality and Persons with Disabilities, Second Annual International Conference, pp. 63–68.*

Lamson, R. Virtual Therapy, Polytechnic International Press. Montreal Canada, Sep. 1997.*

* cited by examiner

VIRTUAL REALITY IMMERSION THERAPY FOR TREATING PSYCHOLOGICAL, PSYCHIATRIC, MEDICAL, EDUCATIONAL AND SELF-HELP PROBLEMS

CROSS-REFERENCE TO RELATED APPLICATION

This application claims the benefit of applicant's provisional patent application Ser. No. 60/049,212, Filed Jun. 9, 1997.

FEDERALLY SPONSORED RESEARCH

None

SEQUENCE LISTING OR PROGRAM

None

BACKGROUND OF THE INVENTION

1. Field of Invention

This invention relates to mental therapy, particularly to such a therapy using a virtual reality environment. The invention will be used in medical, psychiatry, psychotherapy, education, selfhelp, home, and entertainment environments and produced with computer hardware and computer software.

2. Prior Art—Psychotherapy-Psychiatry-Mental Health

Originally prescriptions for mental health came from philosophers. Socrates recommended "know thyself" and this advice formed the core of psychoanalysis and psycho-dynamic treatment approaches. Though these methods permitted patients to know and understand themselves better, they failed to change thinking and behavior in a way that would cure emotional distress and impairment. Aristotle (384–323 BC) was the first person to write a systematic psychological treatise which emphasized that knowledge is gained by experience. Behavioral approaches to psychotherapy attempt to influence patient activities, but fail to explain why knowledge from that experience is not enough to correct it. Cognitive or thinking approaches to psychotherapy propose altering distortions in thinking because these lead to emotional distress. Attempts to influence conscious processes have achieved some degree of success, but patients often resist therapeutic interventions which suggest they should change their ways of thinking. Even when people are able to do so, relapses to painful thoughts and emotional distress are common.

Medical efforts to influence human behavior, mental process, and emotional distress have also relied upon invasive procedures. Trephining was a crude surgical practice of the Stone Age whereby a hole was chipped in the skull of a person who was behaving peculiarly. The procedure presumably was conducted to allow the escape of evil spirits. In the Middle Ages, bloodletting was performed for many physical and mental conditions.

Frenkel, in U.S. Pat. No. 4,327,712 (1982) describes an apparatus used to facilitate viewing of one's facial image under controlled illumination patterns for purpose of either psychotherapy or merchandise selection. Simply allowing patients to view themselves without successfully interacting with the environment does not achieve or provide optimized corrective experience.

ECT or electroconvulsive therapy, as shown by Hyman, in U.S. Pat. No. 4,709,700 (1985), is a procedure that continues in psychiatric practice to produce an electric current through the brain to alleviate profound depression. The procedure is typically unpleasant and occasionally dangerous. Patients treated with ECT complain of memory impairment and disorientation in familiar environments.

The use of psycho-pharmacological medications dominate psychiatric practice today. Pharmacological interventions provide symptom management. Patients report some relief from emotional distress, but also complain about day-to-day life restricting side-effects of the medications. For example, psychiatric medications frequently leave patients with dry mouth, constipation, reduced or suppressed sexual interest, weight gain, bloating, sedation, benzodiazepine dependence and withdrawal, frustration with treatment failure, and dependence on the psychiatrist. Raw data from a survey of psychiatrists reveals the overall success rate with medications in the treatment of generalized anxiety disorder is less than 50%.

Woods, in U.S. Pat. No. 4,762,494 (1988) proposes using a doll-like figure on which tears can be applied or removed to reflect current or past mental states. Similar dolls are readily available in department and toy stores. Given the widespread availability of dolls with varying attributes, the possibility for a child-doll dialogue seems obvious.

An apparatus and method for treating undesirable emotional arousal of a patient is shown by Weathers in U.S. Pat. No. 5,219,322 (1993). This uses visual and auditory stimuli as a crude process for eliciting mental imagery of a negative experience. The apparatus does not correspond to natural human experience where people interact with the environment and with others. The primary goal of psychotherapy is to provide corrective experiences that can be effectively used by patients. The more closely the corrective experience simulates reality, the more effective the treatment. Weathers does not use any fully interactive visual and auditory stimulations that are under the control of the patient. He does not accurately simulate reality or permits the user to influence the environment as well as be influenced by it. His method does not closely correspond to events that occur in reality and thus, cannot be effective corrective learning contexts for patients. His method does not empower users because they are not in control of exposure to every aspect of the environmental experience.

Rodgers, in U.S. Pat. No. 5,403,263 (1995), describes a method for reducing anxiety and recovery time of a patient during preoperative, intra-operative, and postoperative phases of surgery. Unlike virtual therapy interactivity, this procedure is limited by its passive introduction of sound and voice to the patient. He does not provide much opportunity to reduce emotional distress by distraction to pleasant scenes accompanied by an auditory input. Also he does not provide opportunities for patients to recovery faster by viewing successes of others and by rehearsal of activities while immersed in a virtual environment known to facilitate recovery.

Brill, in U.S. Pat. No. 5,435,324 (1995), shows a method and apparatus for measuring psychotherapy progress. The procedure requires administration of questionnaires to patients and may be considered an assessment of the patient's emotional state. However assessment during treatment is difficult to accomplish and requires cumbersome administration, collection, and analysis of paper and pencil tests. There is no verbal feedback during assessment and treatment, nor any description of successes and difficulties during environment encounters.

Rosenfeld, in U.S. Pat. No. 5,450,855 (1995), purports to treat alcohol and drug addiction and in U.S. Pat. No.

5,280,793 (1994) purports to treat depression by brainwave training for the purpose of achieving biofeedback. The patient is rewarded for changing asymmetry. This method of treatment shows little, if any, correspondence to known treatment practices of substance-related disorders and depression. Getting a patient to focus on brain waves de-emphasizes or eliminates the crucial variables known to cause the greatest problems for chemically dependent and depressed people. Those variables include distorted thinking, mood swings, depression, anxiety, cravings, denial, anger and rage reactions, isolation, interpersonal difficulties, family dysfunction, and need for medical detoxification, to identify but a few. He does not offers chemically dependent and depressed individuals any opportunity to achieve mastery experiences. Exposure and interactions are not under the patient's control, any successes cannot be attributed directly to them. A lack of success does not build confidence. A lack of mental shifts from depressive thinking to optimism will not create hope or any motivation for additional successful experience.

Putnam, in U.S. Pat. No. 5,619,291 (1997), discloses an eye-movement desensitization and reprocessing treatment, but this is an awkward way to engage a patient and does not correspond to natural everyday experience. Visual displays elicit negative emotional responses. They are not interactive. There are no corrective visual sensory inputs for patient to use and experiment to achieve positive mastery experience.

3. Prior Art—Education and Self-Help

Dill, in U.S. Pat. No. 4,273,540 (1981), describes a training device for evaluating disorders of brain damaged patients and of patients who have suffered trauma to or disease of the central nervous system. The training attempts to help patients obtain confidence but is limited by the method. This device does not provide effective methods for assessing, preventing, and treating psychiatric conditions or for building self-efficacy. The power of a procedure is generally believed to aid in patient recovery from emotional distress. This device does not permits assessment of the patient while they are immersed in an environment, nor does it allow assessment of neurological strengths and deficits.

Ito, in U.S. Pat. No. 4,573,472 (1986), shows a medical apparatus for autogenic training. The self-help training procedure operates by providing bio-information stimuli. The user is expected to consider that information and alter behavior. This form of education and training is less effective than other self-help methods because it fails to incorporate intermediate variables known to influence human functioning. It does not provide sensory stimulations that evoke thinking distortions (fear), anticipatory anxiety, danger expectations, failure beliefs, physiological reactions (anxiety, deep breathing or holding of breadth, sweating) during exposure. The lack of composite reactions to visual exposure, auditory and tactile stimulations do not permit the practitioner to immediately introduce interventions for the purpose of achieving corrective experience. Variables that influence behavior, such as self-efficacy, cannot be assessed and strengthened during immersion of the patient in an environment. There is no development of mastery experience based upon instillation of learning principles, skill acquisition, and rehearsal.

Densky, in U.S. Pat. No. 4,717,343 (1988), shows a method for conditioning a person's unconscious mind to effect a desired change in behavior. There is no scientific evidence for a map of the unconscious mind or how it may finction. A procedure designed to influence it cannot genuinely claim that some particular or general aspect of the unconscious mind is being influenced because the principles and processes of the unconscious are not well documented with scientific research. This self-help method exposes a person to a video picture appearing on a screen. The procedure claims that the viewer's unconscious mind observes the video and that somehow the viewing conditions a person's thought patterns that alter behavior in a positive way. Even if this claim were correct, the procedure is weak and does not use known learning principles and sensory stimulations to provide individuals with corrective experiences.

4. Prior Art—Virtual Reality Technology

The term "virtual reality" has been used to describe a computer-generated environment. When viewed with goggles or head-mounted display, it provides the user with a three-dimensional, fully interactive experience. A hand-held grip is used to achieve movement or navigation within the environment. As the user turns his or her head, the view changes just as it would in reality. Buttons on the hand-held grip permit the user to experience movement from one location to another, thus adding a sense of reality, to virtual reality. The technology used to produce virtual reality consists of a graphics-generating computer, a head-mounted-display with a tracking device, a hand-held grip, and other sensory input devices. Various products may be used to achieve the experience of virtual reality (Pimentel, K. and Teixeira, K. 1993, Virtual Reality: through the new looking glass. Intel/Windcrest/McGraw-Hill, Inc. New York).

Virtual reality applications have been developed for art, business, entertainment, flight simulators, medicine, and military battlefield operations. Until 1993, medical applications included computed-aided surgery, building designs for handicapped persons, wheelchair equipped with a virtual reality system, rehabilitation, repetitive strain injury, surgical workstation, and teaching aids for surgeons.

Immersive, 3D, fully interactive virtual reality technology was first introduced as part of a psychotherapeutic method by the applicant (1993) in a Department of Psychiatry for the experimental treatment of acrophobia. The integration of virtual reality technology with learning principles and psychotherapeutic strategies was given the trademark Virtual Therapy by applicant in 1993. Virtual Therapy is a trademark for a method of treating acrophobia and other psychiatric conditions by immersion in simulated or virtual environments. Virtual Therapy provides patients with assessment of cognitive, emotional, and physiological functioning. It is also used for prevention and treatment of psychiatric conditions by providing users with corrective experiences. It is more than exposure treatment in a virtual environment and more than imaginal desensitization (Hodges et al., 1995, 1993; Rothbaum et al., 1995 (two refs.); Kooper, 1994; Williford et al., 1993).

Acrophobic individuals may experience phobic symptoms by simply thinking about heights. No exposure is required to produce anxiety, panic, or avoidance. One standard of care for this condition is cognitive-behavior therapy. Distorted thinking significantly contributes to phobic symptoms. A phobia of heights involves the interaction of thinking, behavior, and physiological arousal. Some have correctly diagnosed or evaluated the condition of acrophobia, yet proposed to treat it by exposure to a virtual environment. However, it is not the subjective evaluation that causes anxiety. There is an interaction between thinking, behavior, and physiology that contributes to anxiety. A subjective evaluation may lead to fear, which is different than anxiety. Fear is a thought. Anxiety is a physiological state. Danger expectations may produce fear whereas anxiety expectations may produce physiological arousal (anxiety). So, mere exposure to real or virtual environments is not enough to treat the condition.

A comprehensive theoretical and clinical discussion of fear, anxiety, panic, and acrophobia can be found in Virtual Therapy (Lamson, 1997). Prior studies exposed participants to virtual environments where the opportunity to perceive height and depth occurred. However, the method of treatment was not adequately explained and there was no theoretical or clinical rationale for exposure therapy. It differs from Virtual Therapy (Lamson, 1997) which describes a system of therapy for the treatment of acrophobia and other psychiatric conditions.

Carlin et al. (1997) present a case report to demonstrate the use of immersive computer generated virtual reality (vr) and mixed reality (touching real objects seen in virtual reality) for the treatment of spider phobia. A patient was exposed to virtual spider scenes over 12 weeks with each session lasting a total of 50 minutes. Exposure to virtual reality spiders produced reduction in anxiety with some symptom relief. The case is difficult to assess because of apparent co-existing obsessive-compulsive difficulties. The authors define their intervention as virtual reality exposure therapy. However, no theoretical rationale for conducting 12 treatment sessions with the patient was discussed.

North et al. (1997) reports on a five-session, single-case study, utilizing virtual reality as a desensitization procedure to reduce fear of flying. The authors' three paragraph letter-to the editor failed to cite any research protocol, method of desensitization, or psychological rationale.

A virtual environment trademarked "Detour" (Addison, 1994) was constructed for the purpose of demonstrating the perceptual experience of one person who suffered brain damage from an auto accident. The application was developed for use in the CAVE, a trademark for an immersive room size virtual reality environment located at the University of Chicago. This particular application evokes deep empathy by visual and auditory sensory inputs. The virtual environment presents scenes of art and the impression of walking down a corridor viewing paintings hung on walls. Suddenly wheels screech and a crash and moan are heard. The scene becomes distorted and unclear, signifying the loss of vision and brain damage. Addison actually suffered brain injury. Though the virtual environment was created to dramatize her traumatic experience, it suggests avenues for other uses.

Gould, in U.S. Pat. No. 5,546,943 (1996) proposes use of a visualization system using a computer to provide a patient with a view of their internal anatomy based on medical scan data. The patient acts upon the information in an interactive virtual reality environment by using tools or other devices to diminish a visual representation of an ailment. In doing so, a psychoneuro-immunological response is postulated to occur in the patient for combating and recovering from the disease. The concept is interesting, yet the activation of a psychoneuroimmunological response may be due to any process that builds an individual's self-efficacy. Self-efficacy is a well known psychological variable proposed to account for an individual's conviction that they can achieve or accomplish or perform a certain task.

Jarvik, in U.S. Pat. No. 5,577,981 (1996) describes a virtual reality exercise machine and computer controlled video system. Jarvik's machine produces a virtual reality environment for exercise regimens, exercise games, competitive sports, and team sports. It is also adapted to a user's individual capabilities. It is used to achieve exercise results from rehearsal.

Walker, Lyon, Linton, and Nye, in U.S. Pat. No. 5,584,696 (1996) describe a simulation system for virtual reality experiences such as hang gliding or the like. They describe an embodiment for mechanical support, visual display, and a method for achieving pupil-forming images.

Kitchen and Bird, in U.S. Pat. No. 5,655,909 (1995) describe a skydiving trainer wind tunnel utilizing a non-immersive virtual reality environment produced by viewing film footage of scenarios descending toward the earth. They provide the user with an opportunity to practice emergency procedures. It does not use an head-mounted display for immersion into the virtual environment.

These devices do not use virtual environments for assessment, prevention, and treatment of psychiatric conditions and for conditions not described in the Diagnostic and Statistical Manual of Mental Disorders (DSM-IV, 1994). They do not rely upon the integration of learning principles and psychotherapeutic strategies with any virtual reality technology. They do not use visual, auditory, and tactile sensory stimulation and feedback during user immersion in virtual environments to assist patients in achieving corrective experiences. The lack of instillation of explicit learning principles during virtual environment exposure prevents users from the direct influence of psychological, emotional, and physiological processes for the development of mental health.

The following are the full citations of references given in abbreviated form in the text:

Addison, R. (1995). Detour: brain deconstruction ahead. In: Satava, R. M., Morgan, K., Sieburg, H. B., Mattheus, R., & Christensen, J. P. Interactive technology and the new paradigm for healthcare. Pp. 1–3. IOS Press, Amsterdam, Oxford, Washington, D.C.

American Psychiatric Association (1994). Diagnostic and statistical manual of mental disorders: Fourth Edition. DSM-IV. Washington, D.C.

Carlin, A. S., Hoffinan, H. G., & Weghorst, S. (1997). Virtual reality and tactile augmentation in the treatment of spider phobia: a case report. Behavior Research Therapy, 35(2): 153–58.

Hodges, L. F., Rothbaum, B. O., Kooper, R., Opdyke, D., Meyer, T., North, M., de Graaff, J. J., and Williford, J. (1995). Virtual environment for treating the fear of heights. IEEE Computer 28, 7, pp. 27–34.

Kooper, R. (1994). Virtually present: treatment of acrophobia by using virtual reality graded exposure. Master Thesis in Computer Science at the Technical University of Delft, Netherlands.

Lamson, R. (1989). The effects of a manual-guided cognitive intervention program upon substance abusers. Unpublished dissertation. University of Southern California.

Lamson, R. (1993). The effects of virtual reality immersion on anxiety disorders. Kaiser Foundation Research Institute.

Lamson, R. (1994). Virtual therapy of anxiety disorders: application: VR in psychotherapy. CyberEdge Journal, Issue #20, Vol. 4, No. 2. Sausalito, Calif.

Lamson, R. and Meisner, M. (1994). The effects of virtual reality immersion in the treatment of anxiety, panic, and phobia of heights. Proceedings for Virtual Reality and Persons with Disabilities, pp. 63–68. Second Annual International Conference, Center on Disabilities, California State University, Northridge.

Lamson, R. and Meisner, M. (1995). Clinical application of virtual therapy to psychiatric disorders: theory research, practice. Pre-Conference Workshop, Medicine Meets Virtual Reality #4.

Lamson, R. (1997). Virtual Therapy: prevention and treatment of psychiatric conditions in virtual reality environments. Polytechnic International Press. Montreal Canada. ISBN 2-553-00631-4.

Maier, S. F., Watkins, L. R., and Fleshner, M. (1994). Psychoneuroimmunology: the interface between brain, behavior, and immunity. American Psychologist, 49(12): 1004-17.

Manning, T. R. (1995). The emotional dimension of experience in information environments. In: Satava, R. M., Morgan, K., Sieburg, H. B., Mattheus, R., & Christensen, J. P. Interactive technology and the new paradigm for healthcare. Pp. 231–236. IOS Press, Amsterdam, Oxford, Washington, D.C.

North, M. M, North, S. M., and Coble, J. R. (1997). Virtual reality therapy for fear of flying. Letter to the editor, American Journal of Psychiatry, 154:1, p. 130.

Pimentel, K. and Teixeira, K. (993). Virtual Reality: through the new looking glass. Intel/Windcrest/McGraw-Hill, Inc. New York.

Rothbaum, B. O., Hodges, L. F., Kooper, R., Opdyke, D., Williford, J., and North, M. (1995a). Virtual reality graded exposure in the treatment of acrophobia: a case study. Behavior Therapy, Vol. 26, No. 3, pp. 547–554.

Rothbaum, B. O., Hodges, L. F., Kooper, R., Opdyke, D., Williford, J., and North, M. (1995b). Effectiveness of computer-generated (virtual Reality) graded exposure in the treatment of acrophobia. American Journal of Psychiatry, Vol. 152, No. 4, pp. 626–628.

Williford, J. S., Hodges, L. F., North, M. M, North, S. (1993). Relative effectiveness of virtual environment desensitization and imaginal desensitization in the treatment of acrophobia. Proceedings Graphics Interface, 162, Toronto.

Objects and Advantages

Accordingly, it is one object of the invention to provide a method for treating psychiatric conditions by immersion into virtual reality environments for the purpose of providing corrective experiences.

The term Virtual Therapy was introduced by Lamson (1993) and is used to define a process that occurs when patients are visually immersed in a virtual environment. Since the environment is fully interactive, users engage in activity for the purpose of providing corrective experience to cognitive distortions, emotional distress, and behavioral deficits. Auditory and tactile sensory inputs may be included to enhance a user's sense of reality during immersion. In the case of phobias, psychological distress is maintained by beliefs, appraisal of threat, anxiety, and situational avoidance. Healing occurs when users develop thinking strategies that result in reduction of distress, increased confidence, and approach behavior.

Exposure to Virtual Therapy environments is under the control of the user. During exposure, users encounter situations through visual, auditory, and tactile sensory stimulation. They may influence or be influenced by that environment. Virtual Therapy is a rapid, non-invasive form of immersive, three-dimensional, interactive treatment. Whether used as a therapeutic method by a licensed therapist, mode of education, self-help, or entertainment process, it presents a less-costly alternative to other forms of treatment currently used in psychiatry.

In addition to the above objects and advantages, several additional objects and advantages invention are described in the following factors 1.a to 1.p. and 2.a–2.m below.

1.a. Immersion into a Virtual Therapy environment permits rapid assessment, prevention, and treatment of psychiatric conditions.

1.b. The method of Virtual Therapy combines therapeutic strategies with learning principles to achieve corrective experiences.

1.c. Virtual Therapy combines methods of education and self-help with entertainment in virtual environments to enhance learning.

1.d. Exposure to visual, auditory, and tactile sensory inputs in the virtual environment are under the control of the user or patient.

1.e. Rapid habituation learning evidenced by rate and blood pressure reductions during virtual environment immersion and exposure.

1.f Virtual Therapy is a faster, better, cheaper method of psychotherapy than other existing methods. Treatment of acrophobia shows that patients benefit from one 50-minute session. Avoidance and anxiety are diminished or eliminated to the extent that patients are able to ascend to heights.

1.g. Compared to other known forms of treatment, Virtual Therapy shows approximately 50% savings.

1.h. Virtual Therapy is simpler than other methods of treatment. Direct sensory input and interactivity permit patients to immediately gain skill and relief from painful symptoms.

1.i. The technology of Virtual Therapy can be easily placed in shopping malls, community centers, schools, hospitals, and offices used for therapeutic interventions.

1.j. The method of Virtual Therapy de-emphasizes the notion of pathology known to psychodynamic forms of treatment. Instead, the method emphasizes learning, self-efficacy, mastery experience, and competence in virtual environments. The entertaining and educational components of Virtual Therapy make public access in shopping malls ideal locations for this form of treatment.

1.k. The technology is safe and easy to use. It produces reliable virtual environments with a lasting life cycle.

1.l. Virtual therapy satisfies several existing needs: cost effectiveness and prevention and treatment of alcohol and drug abuse; also it is entertaining, educational, and exciting.

1.m. Hundreds of telephone calls and letters from the United States and foreign countries have been received after news broadcasts concerning Virtual Therapy research. Many of those inquiring about the treatment offer to pay, regardless of cost.

1.n. Virtual Therapy may be combined with newly available wireless technologies. One example of wireless technology is a telephone with an eyepiece that permits a view of the person being called.

1.o. Though virtual reality technology has been used for visualization in flight simulators, games and entertainment, it is newly described here as a complete system of psychotherapy having medical and self-help ramifications.

1.p. The use of Virtual Therapy produced new and unexpected results and in doing so, suggests it may be used for commercial success. It also satisfies a long-felt but unsolved need to provide psychological services faster, better, cheaper and without the stigma of pathology attached to psychiatry departments.

Virtual Therapy is related to cognitive psychology, behavioral therapy, and behavioral neuroscience. The therapy actively involves the patients' visual system. It is structured, time-limited, and has been successfully used in the treatment of specific phobias of the natural environment type, such as acrophobia. Generalization of treatment effects have been reported for conditions coexisting with acrophobia. For example, a substantial number of patients undergoing Virtual Therapy report past psychological trauma related to physical and emotional abuse, abandonment, and terror from living under a dictatorship. Post-treatment evaluation indicate reduced sense of treat from longstanding emotional disabilities. The therapy is based on clinical trials that show that virtual reality can be used to create experiences that influence how people feel, think, and act. When an acrophobic enters a virtual environment by visual immersion using a head mounted display (helmet), he or she immediately interact with the environment.

Patients receive proprioceptive-response feedback from turning the head to scan, for example, a computer-generated room with textured walls and muted lighting. Participants receive more feedback when they press a button on a hand-held grip in order to move in the virtual world, achieving gradual exposure to heights and depths by clicking or continuously pressing the button. To change the direction of movement, the user simply turns his or her head to the desired view and presses a button. Reduction of exposure to aversive stimuli occurs by looking away, moving to a new location in the virtual environment, using distraction techniques, talking or using other sensory input to re-establish contact with reality, or taking off the helmet.

A sense of danger during virtual reality immersion is derived from encounters that elicit fear. An encounter initially increases production of fearful cognitive processing for most people. Acrophobics may dwell on beliefs that emerge and flood their consciousness, such as "I'm not capable. I can't handle it. I'll never be able to get over my fears." These beliefs are enduring for this person. One valuable component of Virtual Therapy is the opportunity to observe, challenge, and change dysfunctional beliefs.

The events that occur during immersion into a computer-generated environment stimulate memory. Some pertain to undesirable experiences. A sense of threat could unfold from memory, exposure, or both. These occur in the same context that also promotes healing. Exposure to phobic stimuli is known to provoke situational-bound anxiety or panic. The rapid onset of distress appears spontaneous. Therapeutic interventions provided at these critical moments can alter patient dysphoria: "Breathe deeply. Stay there long enough to realize you are okay. Look around. You did this successfully a few minutes ago. You can do it again. You are safe. You are capable. You're doing it." Patients achieve mastery experiences in this way, and their confidence grows.

Virtual Therapy gives the user an opportunity to experiment with thinking. Instead of dreading a fall from a virtual bridge perceived to be elevated hundreds of feet above water, the user may pause long enough to become familiar with safety. Safety is achieved by scanning the virtual environment. The patient first considers a location, then scouts out potential directions of travel. Thoughts, feelings, heart rate, and muscle tension are observed during the excursion. Threat and caution give way to experimentation. Moving closer to the side of the bridge and looking over may initially provoke feelings of threat. Yet, within a very short period of time, minutes, the user begins to experience habituation. Tension drains from the patient's physiology (e.g. neck and shoulders) and deep breaths produce a relaxed posture.

Additional Objects And Advantages 2.a. Previous failure of others. Virtual Therapy is a form of treatment that provides exposure under the control of the patient. Previous exposure methods brought the patient into contact with reality in the presence of a clinical practitioner. Flooding is an example of this kind of exposure. Unfortunately, flooding was a crude attempt at desensitizing patients to their fears and phobias that showed varied success. Some patients became more sensitized, more anxious, and more phobic after flooding treatment than before.

2.b. Solves an unrecognized problem. Standard forms of psychotherapy utilize face-to-face visits with a clinician (therapist), group therapy, psycho-educational workshops (classes), and medications (which is an invasive procedure). Virtual Therapy does involve a therapist. But the treatment takes place in a virtual environment where the patient has the opportunity to face challenges and struggles by visual and auditory immersion. Virtual encounters permit the patient to rapidly confront and resolve problems resulting in anxiety, panic, phobias, depression, and chemical dependency.

2.c. Solves an insoluble problem. Transference is a psychological phenomena described in the literature. It is understood to be a relationship problem that evolved from the patient's past experiences but was transferred on to the therapist. It occurs between the patient and therapist. In Virtual Therapy, the patient interacts with the technology and virtual environment. The patient influences the environment and is influenced by it. Thus, transference to the therapist is eliminated because the patient's focus is absorbed by interactions with the virtual environment.

2.d. Commercial success. Virtual Therapy has NOT been offered commercially. However, the success of virtual therapy treatments has received media attention. Therefore, hundreds of calls from across the United States and around the world have been received, requesting treatment. Blue Shield of California is providing alternative health care such as acupuncture, chiropractic and other alternative health care services at discount prices to its 1.6 million California members. In January, 1998, the Blue Shield alternative health care program, called Lifepath, will offer access to a network of more than 1,000 qualified practitioners including massage therapists, stress management experts, and fitness clubs. "Consumers don't always want invasive procedures and Blue Shield is responding to their desire for more choices" said Myra Snyder, president of the California Association of Health Plans. The potential market for Virtual Therapy includes traditional health care subscribers and out-of-pocket payers for alternative care. Blue Shield estimates that consumers spend approximately $10 billion annually (out-of-pocket) on alternative health care services.

Virtual Therapy is a non-invasive procedure. It is currently used experimentally and suitable for other traditional and alternative health care environments as suggested by the Blue Shield Lifepath program.

2.e. Unappreciated advantage. Virtual Therapy is a new form of treatment that occurs when the patient interacts with a 3D computer generated immersive virtual environment which contains varied objects, images, colors, and sounds. A hand-held grip with buttons allows the patient to move forward with a sensation of walking of flying. It will also permit vertical upward or downward movement. The patient can change the environment by moving, adding, removing, enlarging, subtracting, and multiplying the number of objects present. For example, the patient may choose to pick up a chair and move it to another side of the room; turn on a fan; turn the room lights on or off; open a door; add a lamp to a table; drop an object that sounds as if it is breaking. and so on. Collectively, these movements provide therapeutic advantages over other forms of treatment because the patient, then and there, can rehearse and practice tasks previously consider overwhelming, in a safe virtual environment.

2.f. For millennia, healers, shamans, priests, and physicians attempted to call upon "higher powers" and spirits to cure the patient. Visions were reported by those afflicted with emotional distress (William James, Varieties of Religious Experience) Now, in Virtual Therapy, visual and auditory sensory inputs generate images and sounds to influence the patient. The virtual experience captures the imagination of the patient and can be used effectively to heal them.

2.g. Solution of long-felt need. Virtual Therapy solves a long-felt need to clarify the therapeutic process. Compared to other systems of psychotherapy, the process is well defined and can be replicated anywhere to validate treatment results. The personality of the therapist is less important with this form of treatment than others because the patient interacts with the technology to receive corrective experiences. It eliminates arguments about the nature of the cure because it is less the therapist and more the quality of the virtual environment interaction that leads to patient health.

2.h. Contrary to prior art's tea ching. Virtual Therapy contradicts previous notion s that the therapist is all important in therapeutic endeavors because healing was presumed to take place through a transference process. It challenges prescriptions for therapy with someone specialized in psychodynamic, cognitive, behavioral, existential, gestalt or other mode or medium. Virtual Therapy eliminates such conceptualizations and arguments with the use of re-usabl e virtual environments for healing. The virtual contexts are integrated with learning principles for providing each patient with a corrective learning experience.

2.i. Virtual Therapy integrates virtual reality technology with known psychological principles derived from cognitive-behavioral therapies, existentialism, psychodynamic conceptualizations and knowledge based upon behavioral neuroscience, neurobiology and neurophysiology. The resultant form of treatment, virtual therapy, yields results far in excess of the principles specific to each contributing component. The synergistic effect was not anticipated by original pioneers in the fields of computer science and engineering who experimented with virtual reality. (Pimentel K. & Teixeira, K. (1993) Virtual Reality. Inte/Windcrest/McGraw-Hill, Inc., New Y ork).

2.j. Different combination. Virtual Therapy combines technology with learning principles to provide corrective experiences for patients diagnosed with psychiatric and medical difficulties. It may also be used for those not formerly diagnosed yet experiencing difficulties with daily living. The benefits of this form of treatment are documented (Lamson, R., 1997. Virtual Therapy, supra). Virtual Therapy currently utilizes 3D immersion technology, including a head mounted display. As technological innovations advance with the concurrent building of learning principles into virtual environments (for therapeutic change), the delivery of this information through visual sensory input may take varied forms. For example, the visual display may be attached to a phone so that remote access to virtual environments may occur at home, in the office, or in public areas. Cellular technology, combined with a visual display, increases the opportunity to influences conscious processes at remote sites. Virtual Therapy may use video in two dimensions or video in three-dimension immersion using a head-mounted display.

2.k. Prior-art references would not operate in combination. The prior-art of virtual reality, identifying computer technology, graphic displays, hand-held-grip, and graphics (e.g. military applications, flight simulation, NASA COSTAR Mission to repair the hubble telescope) was not enough to suggest application of the individual or collective components for psychiatric treatments.

2.l. The Virtual Therapy method demonstrates that it is an inventive combination of prior art. These include but are not limited to computer technologies that produce graphics (SGI Machines, Division ProVision 100, Pixel Plane Technology), head-mounted displays (Virtual Research Flight Helmut, Division, Eyegen 3, Stereo Graphics Crystal Eyes), hand-held grips (Division Joystick and Logiteck 3D), and software support (Division, DVS) to produce stereo image generation, binaural audio synthesis, collision detection, and integration of a range of peripheral devices such as gloves and head-mounted display systems. Authoring software (Division, dVISE) can be used by non-programmers to import objects for the purpose of building and modifying virtual environments. In addition, knowledge of assessment and treatment of psychiatric conditions from varied psychological perspectives and theoretical backgrounds serves as "psychological software" for the production of virtual environments. Knowledge of vision and the development and influence of perception using psychological principles is findamental to this form of treatment.

Further objects and advantages of my invention will become apparent from consideration of the drawings and ensuing description.

SUMMARY

Virtual therapy differs from the prior art by using virtual environments for assessment, prevention, and treatment of psychiatric conditions and for conditions not described in the Diagnostic and Statistical Manual of Mental Disorders (DSM-IV, 1994). Visual, auditory, and tactile sensory stimulation and feedback during user immersion in virtual environments are used to assist patients in achieving corrective experiences. The instillation of explicit learning principles during virtual environment exposure permit users to directly influence psychological, emotional, and physiological processes for the development of mental health.

Virtual therapy is primarily a psychotherapeutic, psychiatric, medical, educational, and self-help invention for prevention and treatment of psychiatric disorders and for problems not otherwise specified in psychological assessment and diagnostic literature. The process is comprehensive and takes place during immersion in fully interactive three-dimensional virtual reality environments utilizing computer generated graphics, images imported from photographs, and video for sensory stimulation. Immersion is achieved with goggles, a head-mounted-display, or another form of visual stimulation, such as surround projection screens or monitors or devices that permit the user to have a virtual experience. It includes the use of voice, music, and sound and other forms of physiological stimulation and feedback. Body sensors and devices such as a hand-held grip, permit the user to interact with objects and navigate within the virtual environment.

Virtual therapy is psychotherapeutic because it permits assessment, diagnosis, and treatment of cognitive, emotional, and behavioral functioning of the user during immersion in the virtual environment. Virtual therapy is also an educational intervention because principles of learning are built into the method so that the user achieves maximum benefit from the experience. Sensory stimulation is known to influence habituation and sensitization (forms of learning associated with neurons) along the visual pathway. Visual sensory input during immersion in the virtual environment shows promise for assessing and treating medical conditions related to vision, migraine headaches, pain, strokes and other neurological states influenced by learning and memory. Virtual therapy provides opportunities for self-help when the user of a virtual environment is provided with information on how to benefit from the experience or when a provider gives verbal directions on how to benefit from the experience or when the virtual environment itself provides the user with directions on effective use of learning strategies during immersion in the virtual environment.

Virtual therapy is an evolving system of psychotherapy conceptualized before and after clinical trials (Lamson, 1993) (full citations of all references are listed above) using virtual reality immersion technology. It utilizes descriptions of psychiatric disorders from Diagnostic and Statistical Manual of Mental Disorders IV (APA, 1994). It also derives the etiology of disorders from research literature and clinical interviews. It provides therapeutic principles and techniques unique to interventions aimed at reduction of distress, found, e.g., in anxiety, panic, phobias, depression, alcohol and drug abuse/dependence, and somatization conducted in virtual environments.

Virtual therapy includes the assessment of cognitive, emotional, and physiological functioning before, during, and after treatment of psychiatric conditions. Some of the conditions referred include obsessive-compulsive disorder, phobias, depression, panic disorder, migraine headaches co-existing with other psychiatric disorders and others. As a natural extension of treatment and referrals from other practitioners, virtual therapy has conceptualized evaluation and possible treatment of individuals suffering neurological impairments resulting from stroke and brain trauma.

DRAWINGS

Figures

Figure 1:
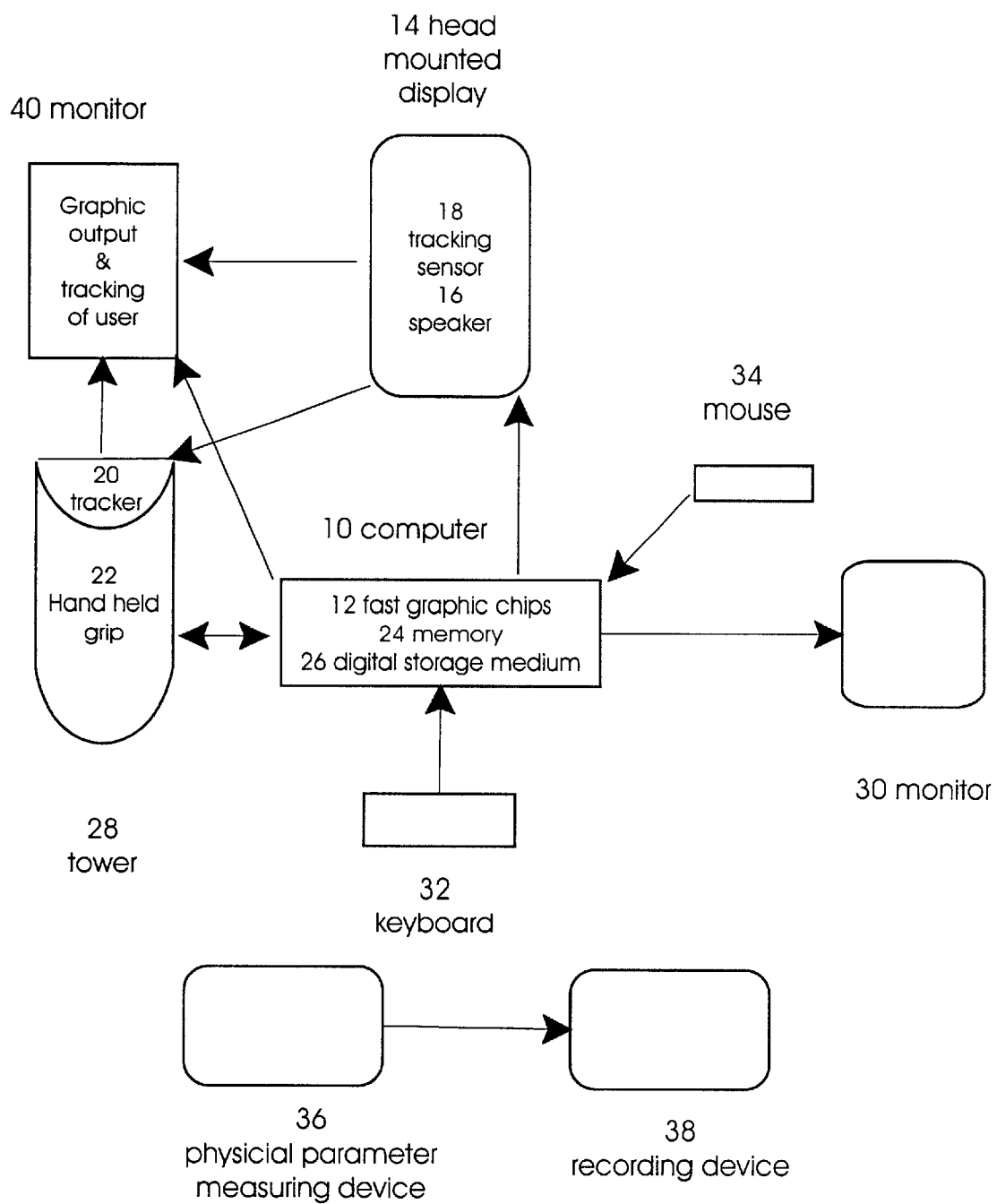
FIG. 1 is a block diagram of a virtual reality computer system employed in the method according to the invention.

| -Reference Numerals | |
|---|---|
| 10. virtual reality computer unit | 12. fast graphic chips |
| 14. head-mounted display | 16. head-mounted display speaker |
| 18. tracking sensor | 20. tracking device |
| 22. hand-held grip input device | 24. computer memory |

| -continued | |
|---|---|
| -Reference Numerals | |
| 26. digital storage medium | 28. tower |
| 30. monitor | 32. keyboard |
| 34. mouse | 36. physical parameter measuring device |
| 38. recording device | 40. monitor (views virtual environment & position of user) |

DETAILED DESCRIPTION

Preferred Embodiment

FIG. 1 shows a block diagram of a preferred embodiment of a computer unit 10 equipped with peripheral technology supporting the production of virtual reality environments for viewing and interaction by the user. At the heart of unit 10 are fast graphic chips 12. In addition to providing the operations necessary to run unit 10, the fast graphic chips produce three-dimensional graphics and can process video data. Of course, in complex systems, the task of producing fast graphics may be provided by a number of chip technologies. In the preferred embodiment of fast graphics technology, the system uses a pixel-plane fast-graphics system, such as that manufactured by Hewlett Packard.

A head-mounted display unit or screen 14 is connected to computer unit 10. The resolution and size of display screen 14 are sufficient to project visual images generated by the computer graphics. In a preferred embodiment screen 14 is a high-resolution visual display. A speaker 16 mounted to the head-mounted display transmits computer generated sounds through ear-phones as well.

Head-mounted display 14 is connected to a tracking sensor 18 which receives and sends data. Tacking sensor 18 receives and sends position location data to a tracking device 20. Tracking device 20 receives and sends the data to computer unit 10. The data is transmitted in a bi-directional manner. When the patient moves or turns or adjusts any part of their body, the result is detected by tracking device 20 and visually shown by a change in graphics generated by computer unit 10 and shown in display 14.

A patient input device 22 is also connected to the computer. Input device 22 can be a hand-held grip, joystick, mouse, button, trigger or the like, or combination of these devices. The input device may also be voice activated through a microphone. A suitable choice of input device 22 is made based upon the use of fully interactive, immersive, virtual reality computer technology 10 and the psychiatric or medical condition of the patient. Input device 22 will thus permit the patient to interact with the computer-generated graphics.

Additionally, computer based unit 10 has a memory 24, which is in communication with the computer's processing capability. Memory 24 contains data required by computer 10. In the exemplary embodiment illustrated in FIG. 1 memory 24 consists of a single unit. However, configurations with memory units of different types are possible. Unit 10 is also connected to a digital storage medium 26 and associated reading device (not shown). Digital storage medium 26 can be a hard disk, floppy disk, compact disk (CD), a cartridge, a network storage unit, or any other standard medium capable of storing electronic instructions for running fully interactive, immersive, three-dimensional graphics on unit 10. The ability to hold a large amount of data is a prerequisite for storing large graphic programs.

The block diagram in FIG. 1 shows a particularly convenient embodiment for implementing the diagnosis and treatment method. Virtual reality computer unit 10, head-mounted display 14, hand-held grip 22 are linked together and produce an output shown on a video display monitor 40. The clinician performs on-going assessment of the patient by observing reactions to the virtual environment. The patient's location within the virtual environment is continuously shown to the clinician on monitor 40. This information permits the clinician to make diagnoses and strategic interventions as needed.

The preferred embodiment also has a plastic tower 28, used to hold the tracking device 20, and hand-held grip 22. A standard monitor 30, keyboard 32, and mouse 34 are used to ready computer 10 for production and display of virtual reality graphics. When computer 10 is ready, a menu showing icons for virtual environments used to treat psychiatric and medical conditions appears on monitor screen 30. For example, when an icon named "VIRTUAL THERAPY of HEIGHTS" is selected, a virtual environment used to treat the psychiatric condition of acrophobia appears and can be seen through display 14.

A physical parameter measuring device 36, e.g., a heart rate and blood pressure sleeve connected to a recording device 38, is used to monitor patient physiological responses during treatment. The choice of the measuring device and recording device is made by the therapist or physician, depending on other hardware intended for patient treatment in virtual reality or virtual therapy environments.

The method of the invention is also useful in the following areas:

Experimental and clinical uses of psychodynamic, gestalt, cognitive-behavioral, and self-psychology conceptualizations for assessment, prevention, and treatment of psychiatric conditions (memory of childhood abuse, failure patterns, and phobic responses).

Biofeedback, hypnosis, neurology (stroke, concussions), ophthalmology, conceived induction states for the purpose of treatment for pain control (e.g., headaches), and their management and relief.

Assessment, prevention and treatment (including induction states) are achieved with visual, auditory, and tactile sensory stimulation with assistance of two- and three-dimensional immersion technologies. Such technologies can include a wireless cellular phone fitted with a visual display; a remote site accessed by means of a television monitor; Internet access; wrist, arm, waist, shoulder, neck, and head fitted devices which are band programmed for random or systematic stimulation at home, in a car, in public transportation, or in public areas which provide access services; and a system for projection of images onto walls, ceilings, or floors that appear to be three-dimensional and real. The user should have the ability to interact with the images.

Operation

Before using the virtual reality-based technology shown in FIG. 1, a patient will first visit a physician or health care professional to evaluate his or her psychiatric or medical condition. The practitioner will diagnose the condition and choose the proper treatment based on patient needs.

TABLE 1. shows the basic processes of virtual therapy which the mental health professional can use for evaluation and treatment of psychiatric conditions such as phobias, anxiety disorders, depression, and substance-related disorders.

Table 1: Basic Processes of Virtual Therapy

Develop Practitioner-Patient Relationship
Identify presenting problem(s)
Obtain history of presenting problem(s)
Collaborate on virtual therapy goals
Agree on commitment to tasks leading to successful achievement of treatment plan
Identify target problems
Discuss principles of learning in immersion
Identify value of immersion rehearsal
Construct associations between choices, emotions, behaviors
Immerse in virtual environment specific to patient presenting complaint(s)
Produce opportunities to confront problems (e.g. anxiety, panic, phobias, depression)
Provide mastery experiences by exposure
Transfer virtual successes to real world
Discuss multiple skills for achieving and maintaining treatment goals
Plan follow-up visit as part of treatment strategy.

Figure 2:
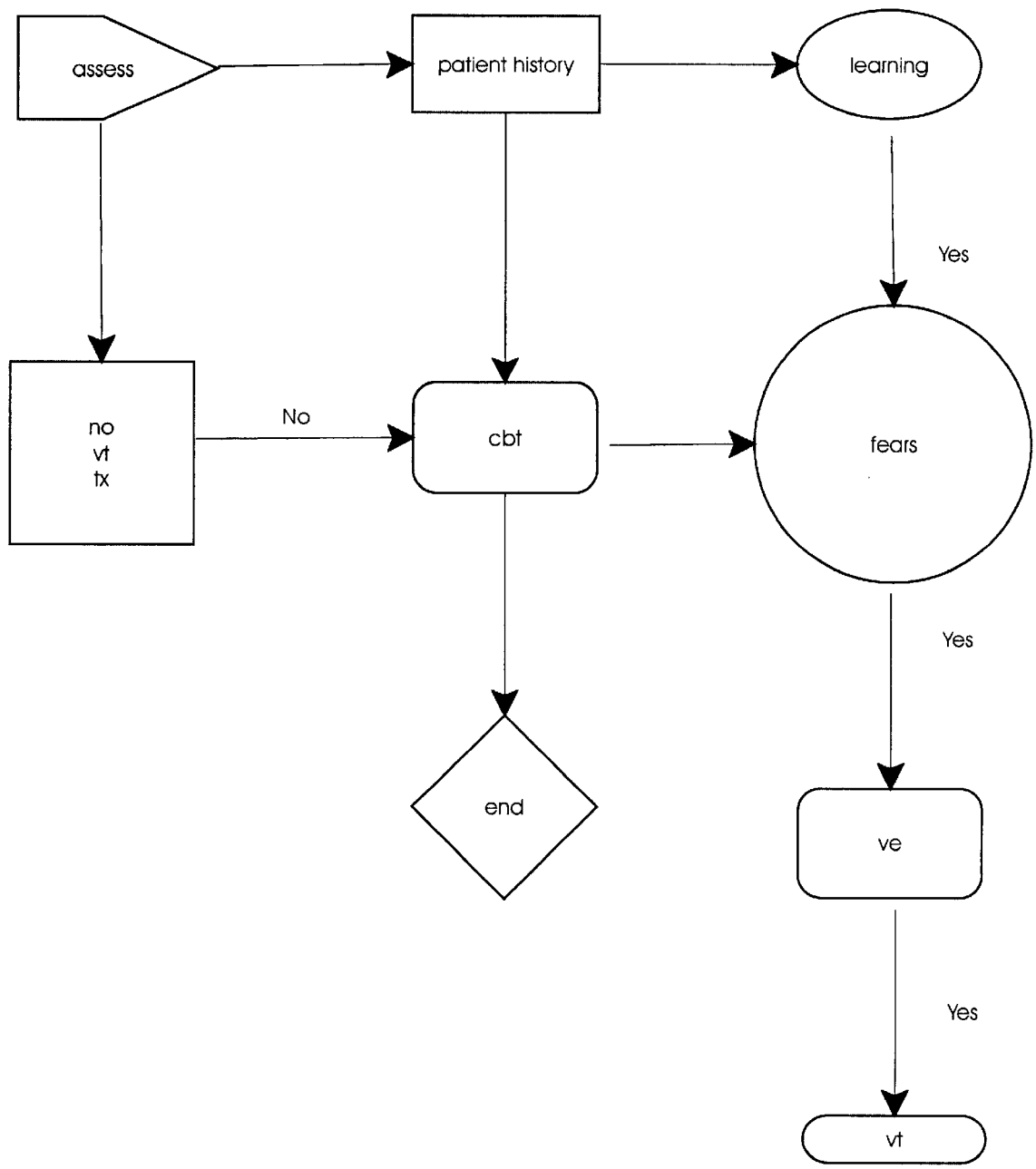
FIG. 2 is a first flowchart illustrating psychological strategies for selecting a virtual enviromnent for common psychiatric and medical conditions.

FIG. 2 shows assessment, history, and psychological strategies which the mental health professional can draw upon for treating phobias, anxiety disorders, depression, and substance-related disorders. The psychological strategies listed include explicit identification of learning principles, cognitive re-framing of distorted thinking processes, and replacement of failure beliefs with success experiences achieved in the virtual environment. Rather than simply distracting the patient's attention away from fear-eliciting environmental cues, such as virtual exposure to heights, the virtual therapy patient is given time to evaluate the effects of exposure on thinking, feelings, and behavior. During evaluation of the immersive virtual experience, when sensory stimulation impacts vision, hearing, and touch, the patient learns cognitive strategies to overcome fears and achieve a conviction that they can positively influence themselves. With practice and rehearsal, newly formed skills and strategies are strengthened through the cognitive mediator of self-efficacy.

As shown in FIG. 2, the patient is first assessed. If they do not have a condition which would be treatable by virtual therapy, they are not given virtual therapy or any treatment ("no vt tx") and then are referred for possible cognitive-behavioral therapy ("cbt"). If the cognitive-behavioral therapy substantially cures the patient, they are finished with treatment ("end"), but if the cognitive-behavioral therapy indicates that the patient appears suitable for virtual therapy, their fears are next assessed; see below.

If the patient appears suitable for virtual therapy, a patient history is taken and if the history indicates that virtual therapy would not be suitable, they are again referred for possible cognitive-behavioral therapy.

If the history indicates that the patient's condition would be suitable for virtual therapy, the patient is taught the principles of virtual therapy in a learning phase ("learning") and then the patient's fears are assessed ("fears").

Next a virtual environment ("ve") is created for the patient and virtual therapy ("vt") is begun The strategies conducted in virtual environments include sensory exposure and interaction, cognitive re-framing habituation, reinforcement, instillation of self-efficacy, rehearsal, role playing, and mastery experience. In addition, the psychological treatment strategies can include methods of counseling and self-help instructions. Compact disks (CD) utilizing non-immersive interactive exposure to virtual environments may form part of the overall treatment strategy. The contents of the CD may include written instructions viewed on a monitor or screen, images and objects to enhance learning and other forms of sensory input to include sound and touch. A compact disk may be used to prepare the patient for three-dimensional, immersive exposure to a virtual environment.

Virtual therapy strategies combine the most appropriate interventions based upon evaluation of the patient's presenting complaints and history. For example, as shown in FIG. 2, the patient's condition may treated with a cognitive-behavior therapy (cbt) intervention to reduce their sensitivity to exposure of feared objects, scenes, and places before immersing them in a virtual therapy environment.

The specific examples below describe exemplary virtual therapy processes used for treating psychiatric, psychological, mental health, medical, educational, and self-help conditions.

Acrophobia—Example 1

Figure 3:
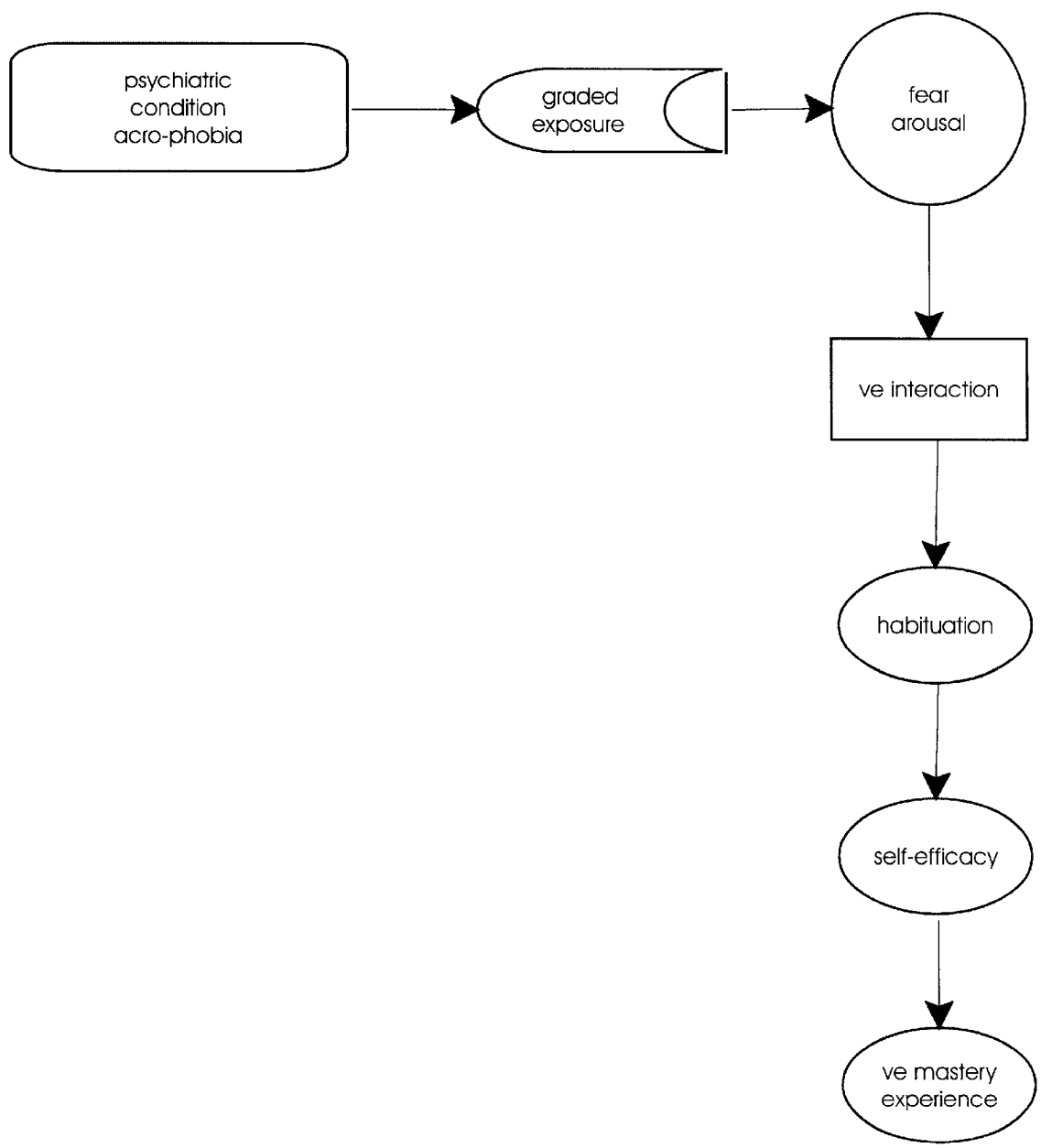
FIG. 3 is a second flowchart illustrating the use of a virtual environment for treating acrophobia according to the invention.

The patient has a severe case of acrophobia (fear of heights). The clinician determines, according to the flow chart in FIG. 3, that graded exposure in a virtual environment under the control of the patient is the best psychological strategy to reduce anxiety and avoidance of heights. The flowchart of FIG. 3 is self-explanatory and outlines the therapeutic steps described below. The treatment utilizes learning, termed habituation, to instill self-efficacy and create opportunity for mastery experiences. Rather than relying upon distraction to reduce emotional distress, the clinician guides the patient through the virtual environment, provides adaptive thinking and emotional management strategies when the patient engages in distorted thinking and behavior based upon failure beliefs.

The acrophobia virtual environment contains graphical representations of a cafe with booths, lighting, textured walls, a bar tap or faucet frequently associated with the delivery of beer, and a walkway between the booths and the bar. A doorway opens to a checkered patio overlooking a bay, hills, and bridge. A plank extends toward but does not connect to the bridge. The space between the plank and bridge reveal a checkered floor beneath. Research participants give varied estimates of depth. Some perceive the distance between the plank and lower to be ten feet while others view it as twenty stories. The bridge has no guardrails. Patients move to the side and look over without falling. The sense of threat and risk are reduced by these experiences. Additional exposure to heights is given to patients. Some use the hand-held grip buttons to rapidly move across the bridge, off the bridge, across the bay, under and over the bridge to deepen a sense of confidence that reduces a sense of danger.

The acrophobia virtual environment produces an audio output through earphones 16 (FIG. 1) contained in head-mounted display 14. Voice, music, and environmental sounds are used to enhance the patient's sense of reality. It is also used to make virtual therapy interventions. The audio output is triggered by the patient's actions in the virtual enviromnent. For example, newage music plays inside the cafe of the acrophobia virtual environment. When the patient enters a doorway leading outdoors, an invisible trigger stops the music and produces sounds of wind and ocean waves. The purpose for this change is to engage the patient's sensory experiences. The sounds create another environmental challenge that the patient must learn to cope with and overcome. When visual and auditory inputs produce mastery performance with increased self-efficacy, the patient has accomplished significant goals during the virtual therapy application for acrophobia.

There are three significant virtual therapy events that contribute to the remission of symptoms associated with acrophobia. The first event begins with immersion of the patient in a virtual environment where they encounter the perception of height and depth. The second event occurs when physiological measures (heart rate and blood pressure) and behavioral observation indicate the patient has habituated with repeated exposure to visual stimuli that elicit fear and anxiety. The third event combines instillation of self-efficacy, mastery performance in virtual reality, and real world performance success. During a pilot study, approximately 90 percent of volunteer acrophobia research subjects reported elimination of avoidance and reduced anxiety and panic associated with fear of heights (Lamson, 1997). 38 volunteers were randomly assigned to one fifty-minute session of virtual therapy.

An analogous virtual therapy strategy is followed in dealing with other anxiety, mood, and substance-related disorders, and also applied to adolescent substance-use prevention, and self help applications.

Anxiety Disorders—Example 2

Figure 4:
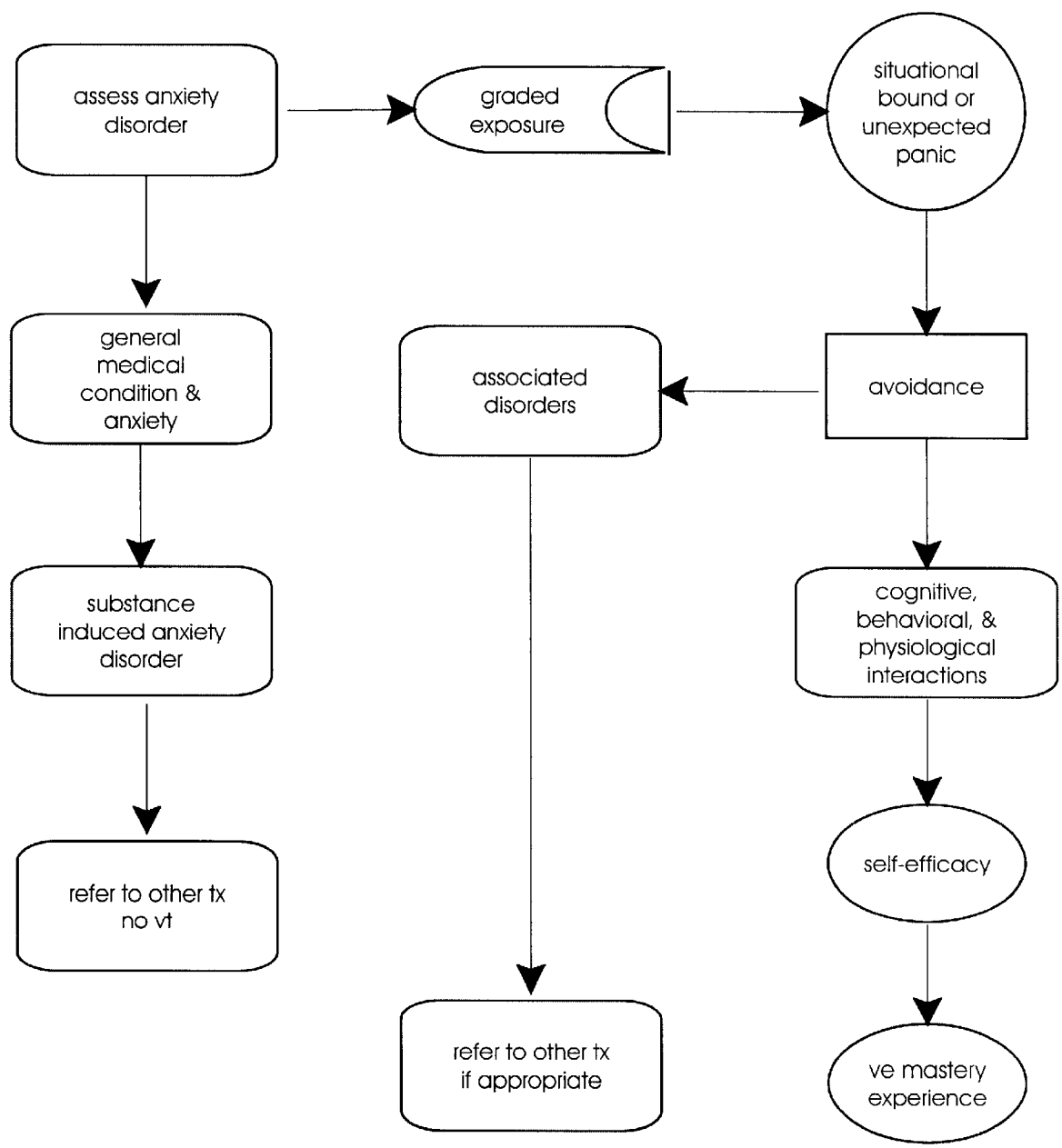
FIG. 4 is third flow chart showing how a virtual environment is used for treating other anxiety disorders according to the invention.

The clinician diagnoses the patient with an anxiety disorder, such as claustrophobia or other specific phobias, panic disorder with and without agoraphobia, social phobia, obsessive-compulsive disorder, post-traumatic stress disorder, acute stress disorder, generalized anxiety disorder or similar disorders. The condition requires a psychological treatment strategy to help the patient cope with their condition. By following a similar process indicated in FIG. 2, specifically according to the flow chart in FIG. 4, the clinician recommends graded exposure in a virtual environment. The flowchart of FIG. 4 is self-explanatory and outlines the therapeutic steps described below. Since virtual therapy provides a finally interactive, three-dimensional, immersive experience under the control of the patient, it is considered the best psychological strategy to reduce anxiety. The treatment uses learning, termed habituation, to instill self-efficacy and create opportunity for mastery experiences. Rather than relying upon distraction to reduce emotional distress, the clinician guides the patient through the virtual environment, providing adaptive thinking and emotional management strategies when the patient engages in distorted thinking and behavior based upon failure beliefs.

The inventive method uses the basic processes of Virtual Therapy in Table 1. The degree of learning and effective use of a virtual environment for treatment of anxiety disorders will determine how people feel and behave in reality. Initial immersion is achieved with a head-mounted display. During the first few minutes of a virtual environment exposure, user heart rate and blood pressure typically increase and a baseline is recorded. Perception of objects or situations may further heighten physiological measures. Cognitive processing during self-report permits in vivo intervention when users perceive danger, experience anxiety, and make attempts at self-protection, such as squatting close to the floor while extending the arms and hands to prevent falling. Judgments about personal experience reflect perceptions of danger and safety, coping, and confidence. Visual cues within the virtual world may elicit a range of perceptions, memories, and emotions. The user may behave with confidence or show a tendency to withdraw.

User reactions to virtual scenes vary. A view of heights from the same vantage point elicits fear from some users and detached interest from others. The degree of sensitivity shown may reflect visual acuity, stereographic perception, genetic predisposition, associative learning, and personality. Eyes converge differently in fixating objects at different distances. Exposure to virtual environments with the intention of challenging dysfunctional cognitive processing and beliefs may have the impact of altering maladaptive reactions to people, places, and objects. How does a virtual therapy theory account for changes in behavior? Variables that contribute to change include prior experience, virtual contexts, mediating, and action-based variables. Self-efficacy beliefs have been shown to predict behavioral change that result from different forms of treatment. When people estimate personal efficacy for accomplishing a task, they do so with inference. Familiarity with the task, required skills, effort, assistance, context, and past experience contributes to the degree of confidence that is perceived.

According to social learning theory, strong personal motivation will overcome obstacles presented by situational factors. If that were true, the annual prevalence of phobias would be reduced from millions to a few isolated cases. When people experience success in virtual therapy contexts, they directly attribute coping and performance to themselves. The virtual therapy process results in greater confidence to achieve reality-based goals than before treatment.

Patients who participated in Virtual Therapy for acrophobia (Lamson, 1993, 1994, 1995, 1997) were able successfully to reduce anxiety and avoidance of heights after one 50-minute session. The Virtual Therapy method of treatment (Lamson, 1997) relies upon a theoretical and conceptual background which integrates virtual reality technology with learning principles and psycho-therapeutic strategies.

Mood Disorders—Example 3

Figure 5:
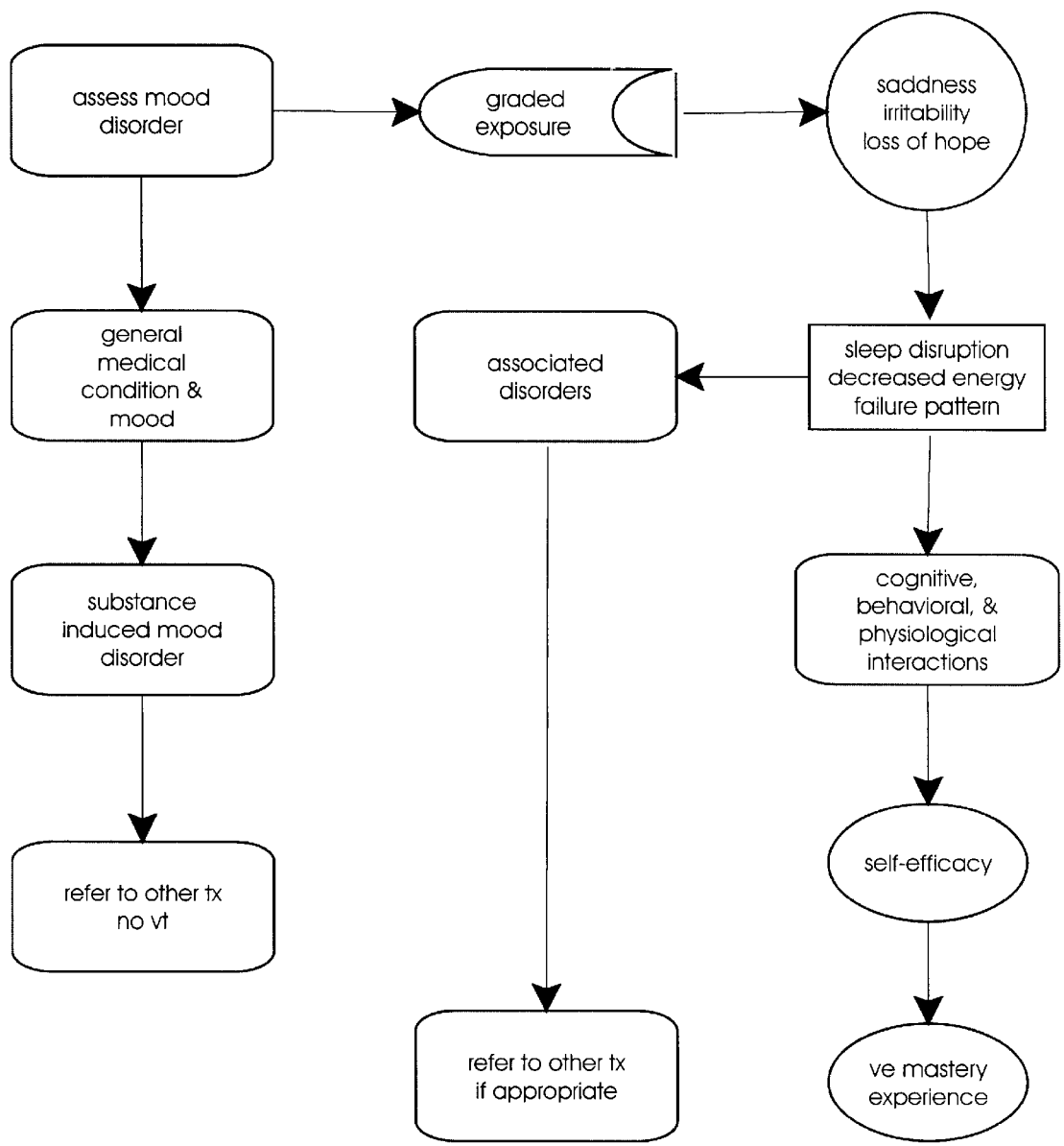
FIG. 5 is a fourth flowchart illustrating the use of a virtual environment for treating mood disorders according to the invention.

The clinician determines, according to the flow chart in FIG. 5, that graded exposure, skill development, instillation of hope, and behavioral interaction in a virtual environment under the control of the patient is the best psychological strategy for learned helplessness mood disorders. The flowchart of FIG. 5 is similar to that of FIG. 4 and is also self-explanatory; it outlines the therapeutic steps described below. Some individuals may experience anxiety and depression within a short period of time and cycle between the two. One form of Virtual Therapy for this condition includes several sensory feedback mechanisms in the virtual environment. Strategic sensory inputs can be used to interrupt negative cognitive processing. These interventions are initiated for the purpose of establishing a perception of reality containing hope and optimism.

Sensory stimulation in virtual contexts is more than a simple exposure or distraction technique. It is a psychotherapeutic, educational, medical, and self-help process. Making shifts in cognitive processing from those that contribute to distorted perceptions to ones of confidence results from patient interactions with virtual objects. Also, exploration of the environment, and replacement of danger (anxiety, panic) evaluations and expectations of loss (depression) with acknowledgments of success based upon performance accomplishments in the virtual context contributes to mastery of the virtual context and provides immediate relief.

An information-processing analysis (Ingram, 1984) of affective disorders suggests that the experience of depression can be viewed as an activation of affective structures referred to as "depression emotion" paths. Once these are activated, the individual continues to experience depression because depression is recycled. The information-processing view of depression has emerged, together with recent theoretical formulations regarding the etiology and maintenance of depression. The most influential theorists of depression to date have been those who conducted research in support of their conceptual and theoretical formulations.

According to these theoretical formulations, depression is a consequence of stresses evoking schemas that code the individual's experience in a negative fashion. Beck termed the depressed individual's distorted view of perceptual experience a cognitive triad, in which the individual sees the future, the environment, and himself or herself negatively. In contrast, Lewinsohn (1974) proposed that depression is due to a decrease or unavailability of positive reinforcement from the environment and that the individual feels unable to alter these conditions.

Rehm (1980) departed from Beck and Lewinsohn by suggesting that the major factor in depression is self-control. According to Rehm's theory, depression results from (1) selective monitoring of negative events, (2) selective monitoring of immediate as opposed to delayed consequences of behavior, (3) stringent self-evaluative criteria, (4) inaccurate attributions of responsibility, (5) insufficient self-reward, and (6) excessive self-punishment. In Seligman's (1974) reformulated the learned helplessness theory of depression in which depression is viewed as a result of an individuals' belief that no matter what they do, their actions will have no impact (response-outcome non-contingency). Depression is believed to be maintained by the individual's internal, global, and stable attributions for failure, while holding external, specific, and unstable attributions for success.

Taken together, these theories attempt to provide a complete and comprehensive account of the psychological aspects of depression. When depression is viewed as a co-existing condition of a substance-related disorder, effective intervention is crucial to the patient's attainment of abstinence. Major theories of depression are supported by research. Each describes the onset of this condition from different points of view. In an attempt to assess which theory most adequately accounts for depression, literature reviews point out that the various theories focus on different aspects of depression, such as perception, attribution, reinforcement, and self-control processes.

One inference made from the information-processing analysis of depression is as follows:

Assume that dual-diagnosis patients or those diagnosed with co-existing psychiatric conditions (e.g., substance dependence and mood or anxiety disorder), participate in group therapies requiring them to recall emotion-laden experiences and substance abuse. In such a situation they will continue to recall these experiences and remain depressed.

Substance-Related Disorders—Example 4

Figure 6:
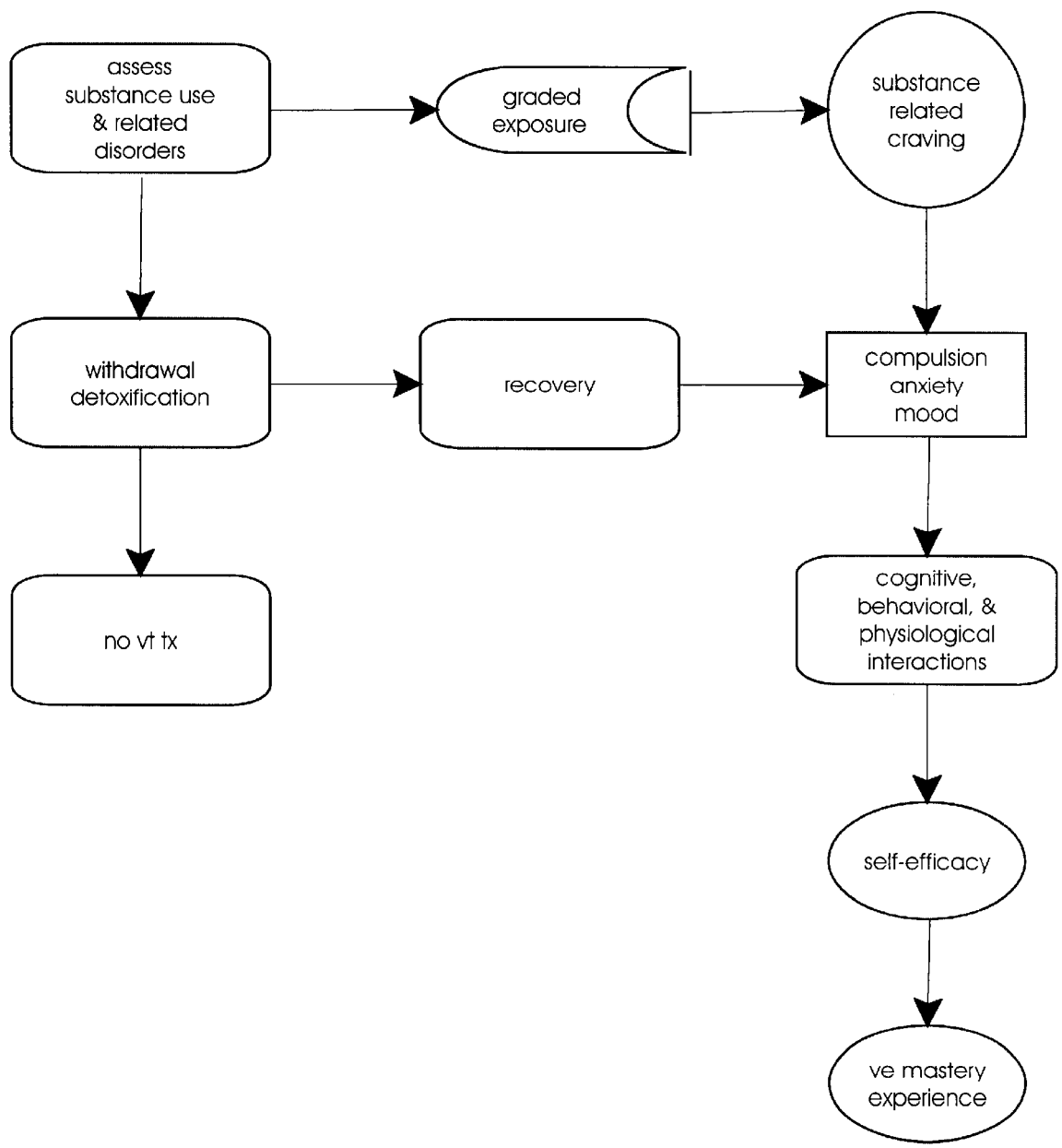
FIG. 6 is fifth flowchart showing how a virtual environment is used for treating substance-related disorders according to the invention.

The clinician determines, according to the flow chart of FIG. 6, that for substance-use disorders, the best strategies are exposure-producing craving and coping skills, management of compulsion, anxiety, and mood, and interactions in the virtual environment to establish self-efficacy. The flowchart of FIG. 6 is similar to that of FIGS. 4 and 5 and is also self-explanatory; it outlines the therapeutic steps described below. Substance-related disorders are described in the Diagnostic and Statistical Manual of Mental Disorders (APA, 1994). Assessment of substance dependence includes evaluation of cognitive, behavioral, and physiological functioning. The reason for seeking treatment, known as the presenting complaint, is discussed at the first interview with each patient.

The first contact with a chemical dependency service usually occurs when a crisis or disturbing event happens.

Co-existing conditions, such as anxiety and depression, are evaluated during the initial assessment interview. The treatment of substance-related disorders is described in the literature (Lamson, 1989). In health-maintenance organizations, individuals entering outpatient early-recovery programs participate in group therapies, attend alcohol and drug abuse education, and go to support groups such as Alcoholics Anonymous. When appropriate, they are provided with detoxification. Disulfiram, sold under the trademark Antabuse, by Ayerst, Mckenna & Harrison Limited Corp., New York, a medicinal preparation for the treatment of alcoholism, is prescribed to a limited number of people as a behavioral insurance policy against drinking. Individual, couple, and family therapy may be part of the recovery treatment plan. Intensive outpatient programs, residential treatment, and hospitalization may be required.

Virtual Therapy for chemical dependency adds a behavioral component missing from other forms of substance-abuse treatment. Immersion in virtual environments offers people "as if" experiences. Patients seeking treatment for dependence on alcohol, marijuana, methamphetamine, cocaine, and other substances report binge and maintenance histories. The frequency and strength of compulsive "using" is related to patient denial. For instance, one patient, having received his fourth DUI (driving under the influence) citation with a blood-alcohol level of 0.32, denied having problems with alcohol. "I'm here because of a court order," he said. As the evaluation proceeded, he disclosed that previous attempts at abstinence had failed. "I can do this on my own," he insisted. "Yes, but didn't you say previous attempts to quit didn't work? "True," he admitted. From initial evaluation, early- and long-term-recovery patients struggle with subtle yet pronounced effects related to alcohol or drugs.

Denial is one way that people protect themselves from reality. It is a form of negative reinforcement. When Jake continued to drink to avoid a painful discussion with his alcoholic mother, he was negatively reinforced. In situations where behavior prevents the occurrence of an aversive experience, it is termed negative reinforcement. A person may deny the occurrence of thoughts such as "I really am a failure. I can't quit drinking. People hate me." Feelings of loss or threat may also be denied. More specifically, discomfort associated with compulsion, craving, anxiety, depression, anger, stress, and other problems may be denied and temporarily subdued with alcohol or drugs.

Denial, as a cognitive process, can be stimulated in virtual environments for the purpose of treatment. As the patient scans the virtual cafe, he sees spigots for draft beer. He has a choice of approaching the counter and drawing a beer or leaving the room. Attempting to draw a beer alters the virtual environment: suddenly, the patient finds himself precariously near a cliff. The sense of threat motivates him to step backward. The therapist points out that the patient has other choices and asks if he wants to try again. "Whew. Yes." This time, the patient passes by the alcohol options and heads toward a doorway with scenic views. He breathes more easily. Positive reinforcement within virtual environments can be established in this way when the user is reinforced for specific choices and actions.

The patient's choices during virtual exposure result in negative and positive associations. The strength of learning accomplished by immersion is that thinking is engaged to reflect upon feelings and behavior. Denial is challenged because the patient has direct and immediate sensory feedback concerning consequences of choices. A variety of experiences can be arranged in virtual environments to provide educational and therapeutic encounters for the purpose of instilling a desire to achieve abstinence and a commitment to maintain it. Rehearsal and mastery experiences can be attained when patients use visual and auditory sensory feedback in the virtual environment. The co-existence of anxiety and depressive conditions with substance-dependence disorders can be targeted for intervention during immersion; the generalization of effects is a distinct possibility when Virtual Therapy is applied to chemical dependency. Table 2 summarizes the virtual therapy concept of chemical dependency treatment.

Table 2: Virtual Therapy of Chemical Dependency

Develop relationship
Obtain history of substance abuse and dependency
Collaborate on virtual therapy goals
Agree on commitment to abstinence
Identify target problems
Discuss principles of learning in immersion
Identify value of immersion rehearsal
Construct associations between choices, emotions, behaviors
Immerse in virtual environment
Produce opportunities to confront denial and avoidance
Provide mastery experiences by exposure
Transfer virtual successes to real world
Discuss multiple skills for achieving and maintaining abstinence Virtual Therapy fits within a bio-psycho-social model of chemical dependency. The model identifies factors that contribute to addiction, which include genetic predisposition, cognition, behavior, personality, family, and other social influences. Recent etiological studies suggest that the processes leading to addiction reside within the brain. Communication between nerve cells in the brain occurs when chemical messages are transmitted across synapses, structures that connect neurons to one another. Substances called neurotransmitters are passed from transmitter neurons to receptor neurons (Shepard, G. M. 1994. Neurobiology, $3^{rd}$ ed. New York: Oxford University Press). During the process of activation, neurons may be altered and changed. Some changes are transient, such as the increase or decrease of the neuron's responsiveness to messages. Other changes in receptors may be long-term, influencing growth, learning, and adaptation. Long-lasting adaptations to alcohol are thought to occur through alteration of the structure and function of specific receptors that have roles in intoxication, reinforcement, and physical dependence.

When the neuron's environment is altered with alcohol, the transmission of information, termed signal conduction, may be changed. "Any alteration in the function of message reception or transduction systems may have significant effects on the progression of alcoholism after drinking has started." (NIAAA, No. 33, 1996, page 2). Research of these mechanisms is underway for purpose of developing pharmacological interventions. "Medications can theoretically be developed to block receptors or enhance their function; to increase or decrease the synthesis, release, or synaptic concentration of neurotransmitters; or to modulate signal transduction" (NIAAA, No. 33, 1996, page 2). The development of medications for alcoholism has two goals: the management of withdrawal and relapse prevention. The neurobiology of addiction is considered because medication interventions targeting brain structures (neurons) for some psychiatric disorders have also been implicated with alcoholism. The question of how best to influence functioning of a person has profound implications for health promotion, prevention efforts, interventions, and recovery from addiction.

Virtual Therapy interventions are also intended to produce changes through sensory stimulation. This discussion is relevant to this section because neuroscientists, psychologists, computer scientists, and engineers are working toward the development of various technologies, from medications, cognitive-behavior and insight therapies, to computer graphics for the delivery of treatments for psychiatric conditions. During treatment sessions, patients frequently disclose anticipatory fear of people, places, and things. Fear is a cognitive process, occurring during appraisal of past, present, and future circumstances. Cognitive, behavioral, and pharmacological treatments have been developed to influence neurobiological functioning by reducing or eliminating exaggerated fear reactions such as panic. Habituation, "a neural mechanism activated by repetitions of a stimulus that reduce the magnitude of responses elicited by the stimulus" (Domjan & Burkhard, 1982, page 342), is one result of such interventions. Panic may be appropriate to a situation or totally unrealistic. In either case, the patient feels distressed. Whether fear is generated from unrealistic expectations or from reality based circumstances, people can enter virtual environments for the purpose of pursuing behavioral options that lead to reduction of stress. Choices made during immersion contribute to the development of thinking skills.

People enter relationships, change jobs, create health risks, and then enter treatment programs, where they learn to stop behaving compulsively and to seek balance for a more enjoyable life. All humans are capable of behaving compulsively in familiar ways, such as eating, drinking, taking drugs, working, gambling, sex, sensation seeking, and exercise. Some people think of these activities but do not act on them compulsively. Others do think about them and act on those thoughts over and over again. Compulsion develops with repetition, rehearsal, and practice. Erasmus said, "Habit is overcome by habit." In Virtual Therapy, people have opportunities to develop new styles of thinking and behaving in safe environments in order to develop healthy habits that can be transferred to reality.

Adolescent Substance-Use Prevention—Example 5

Figure 7:
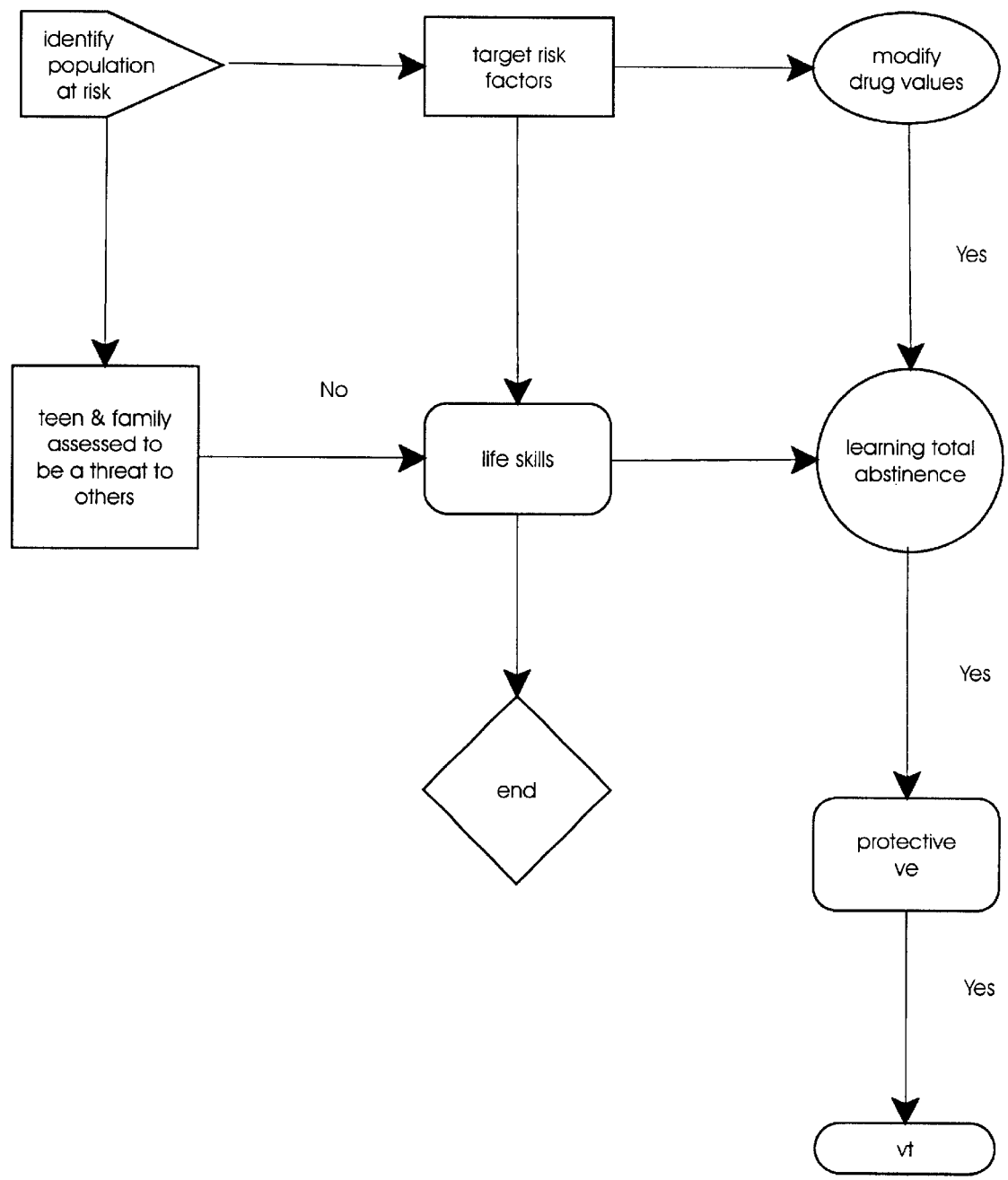
FIG. 7 is a sixth flowchart illustrating adolescent substance-use prevention strategies in a virtual environment according to the invention.

The clinician determines, according to the flow chart in FIG. 7, that exposure which targets adolescent risk factors so as to modify drug values, while simultaneously reinforcing abstinence is the best strategy for prevention of adolescent substance-use disorders. The flowchart of FIG. 7 is similar to that of FIGS. 4 to 6 and is also self-explanatory; it outlines the therapeutic steps described below. Virtual Therapy prevention strategies for substance abuse and dependence focus upon individual perceptions. Interventions conducted in virtual environments rely upon visual perception to produce cognitive experiences. Attribution, reinforcement, skill, mastery, and self-control are goals of such interventions. During immersion in virtual environments, patients' cognitive processing, emotional reaction, behavioral choices, and physiological processes are observed and identified for intervention. Failure beliefs are challenged in vivo, while success experiences are reinforced. Mastery experiences are developed during exposure to activate the user's sense of self-control.

Anxiety disorders, mood disorders, psychoactive substance use disorders share similar diagnostic criteria, despite having different origins and treatments. They often share identical neurotransmitter pathways and treatments options. Because patients may exhibit symptoms shared with other disorders, it is important carefully to differentiate those characteristics of psychiatric disorders and those of psychoactive substance use disorders. The determination of a primary diagnosis is important to treatment. If one diagnosis concerns addiction, then it must be treated before effective management of coexisting disorders can be undertaken. Virtual Therapy shows promise in the treatment of co-existing disorders.

Current evidence suggests genetic, personality, and cultural factors influence the etiology of alcoholism. Diagnosis of the co-existing anxiety and mood with substance-related disorders suggests people are motivated to self-medicate. Virtual Therapy is a promising treatment for substance dependency because the process and technology provide immersive in-vivo experiences for learning. Anxiety, mood, and psychoactive substance-induced disorders often share identical neurotransmitter pathways and treatment options. During exposure, issues concerning denial, compulsion, mood, and behavior can be targeted for intervention. In 1994, drug use among high school seniors increased after a ten-year decrease. Use of illicit substances interferes with school and increase accidents. Use contributes to criminal activity, legal problems, unsafe-sex practices, family conflict, emotional problems, neurologic damage, and experimentation with more harmful substances. High school primary prevention programs emphasize "life skills" and have shown effectiveness over the short term (less than one year). Effective prevention must raise awareness in the adolescent by the steps outlined in Table 3:

Table 3: Virtual Therapy Prevention Strategies

Develop relationship
Obtain history of substance abuse and dependency
Collaborate on virtual therapy goals
Agree on commitment to abstinence
Identify target problems such as school performance, attention, peer and parent relationships, abuse of substances, and mood and anxiety experiences
Discuss principles of learning in immersion
Identify value of immersion rehearsal
Construct associations between choices, emotions, behaviors
Immerse in virtual environment
Demonstrate negative consequences to substance use
Produce opportunities to confront denial and avoidance
Provide mastery experiences by exposure
Transfer virtual successes to real world
Discuss multiple skills for achieving and maintaining abstinence Individuals experiencing negative emotional states are expected to seek relief from this condition and may do so through substance abuse. Based upon current cognitive conceptualizations and neurobiological research, the treatment of addiction and underlying conditions is achieved with a model that emphasizes learning, as do the cognitive and virtual therapies. Virtual Therapy may provide the most effective form of prevention for adolescent substance-related disorders because choices made during immersion in virtual environments have direct consequences. Successful task performance in a virtual context will be rewarded with sensory stimulation that provides pleasant and desirable experiences (consequences). The patient will learn that choices can result in effective behavior and that this behavior will be rewarded. The use of Virtual Therapy in the prevention of substance related disorders is integrated with known successful strategies that benefit those in recovery.

Self-Help Virtual Environment—Example 6

Figure 8:
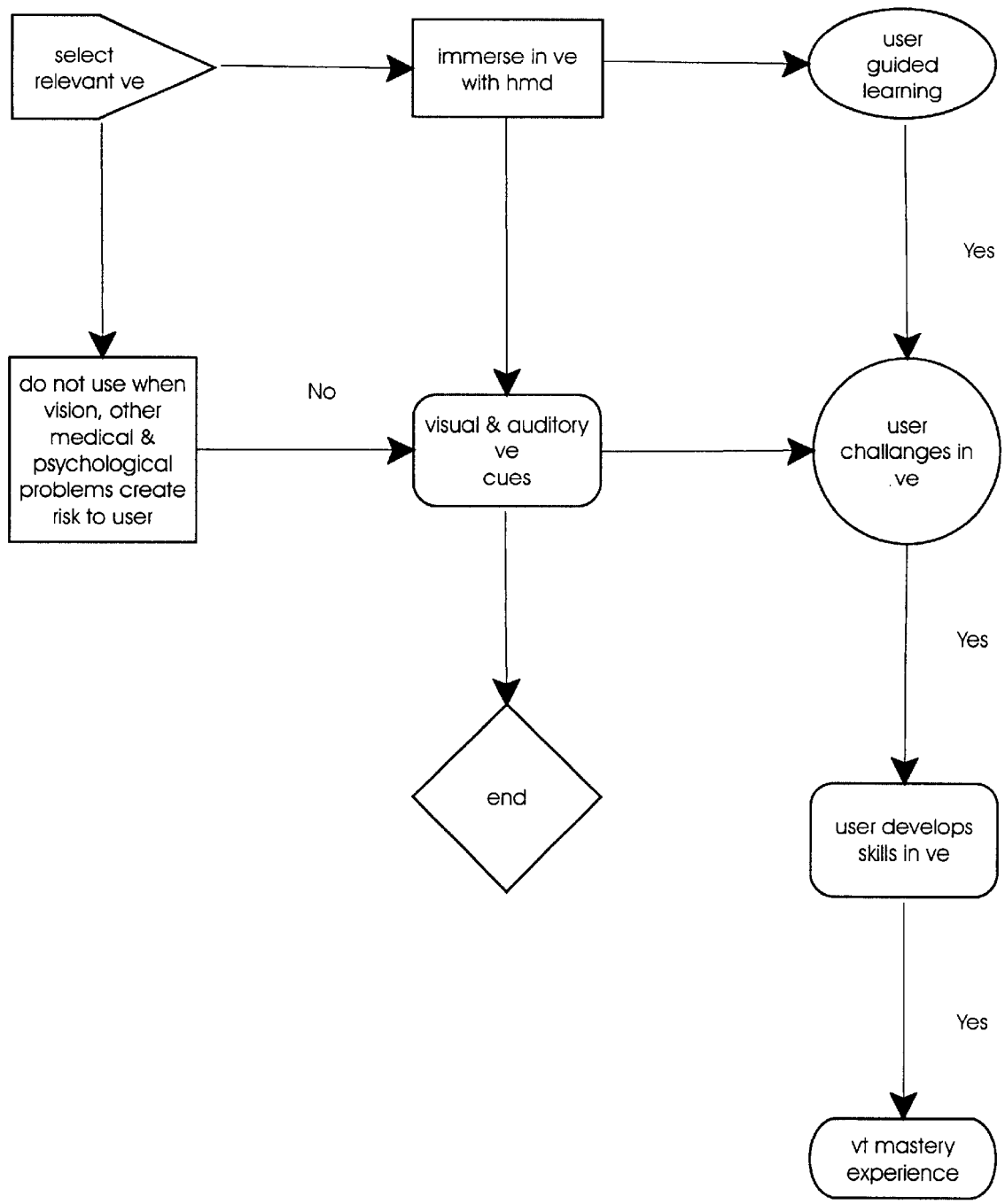
FIG. 8 is seventh flow chart showing self-help strategies in a virtual environment according to the invention.

Virtual therapy is used as a self-help invention, as shown in FIG. 8, for problems not otherwise specified in psychological assessment and diagnostic literature. The flowchart of FIG. 8 is similar to that of FIGS. 4 to 7 and is also self-explanatory; it outlines the therapeutic steps described below. The process is comprehensive and takes place during immersion in fully interactive three-dimensional virtual reality environments utilizing computer generated graphics, images imported from photographs, and video for sensory stimulation. Immersion is achieved with goggles, a head-mounted-display, or other form of visual stimulation, such as surround projection screens, monitors, or other devices that permit the user to have a virtual experience. It includes the use of voice, music, and sound and other forms of physiological stimulation and feedback. Body sensors and devices, such as a hand-held grip, permit the user to interact with objects and navigate within the virtual environment.

Virtual Therapy is a self-help and educational intervention because principles of learning are built into the method so that the user achieves maximum benefit from the experience. Virtual Therapy provides opportunities for self-help when the user of a virtual environment is provided with information on how to benefit from the experience. This benefit also occurs when a provider gives verbal directions on how to benefit from the experience. It further occurs when the virtual environment itself provides the user with directions on the effective use of learning strategies during immersion in the virtual environment.

Medical Uses Virtual Environment—Example 7

Figure 9:
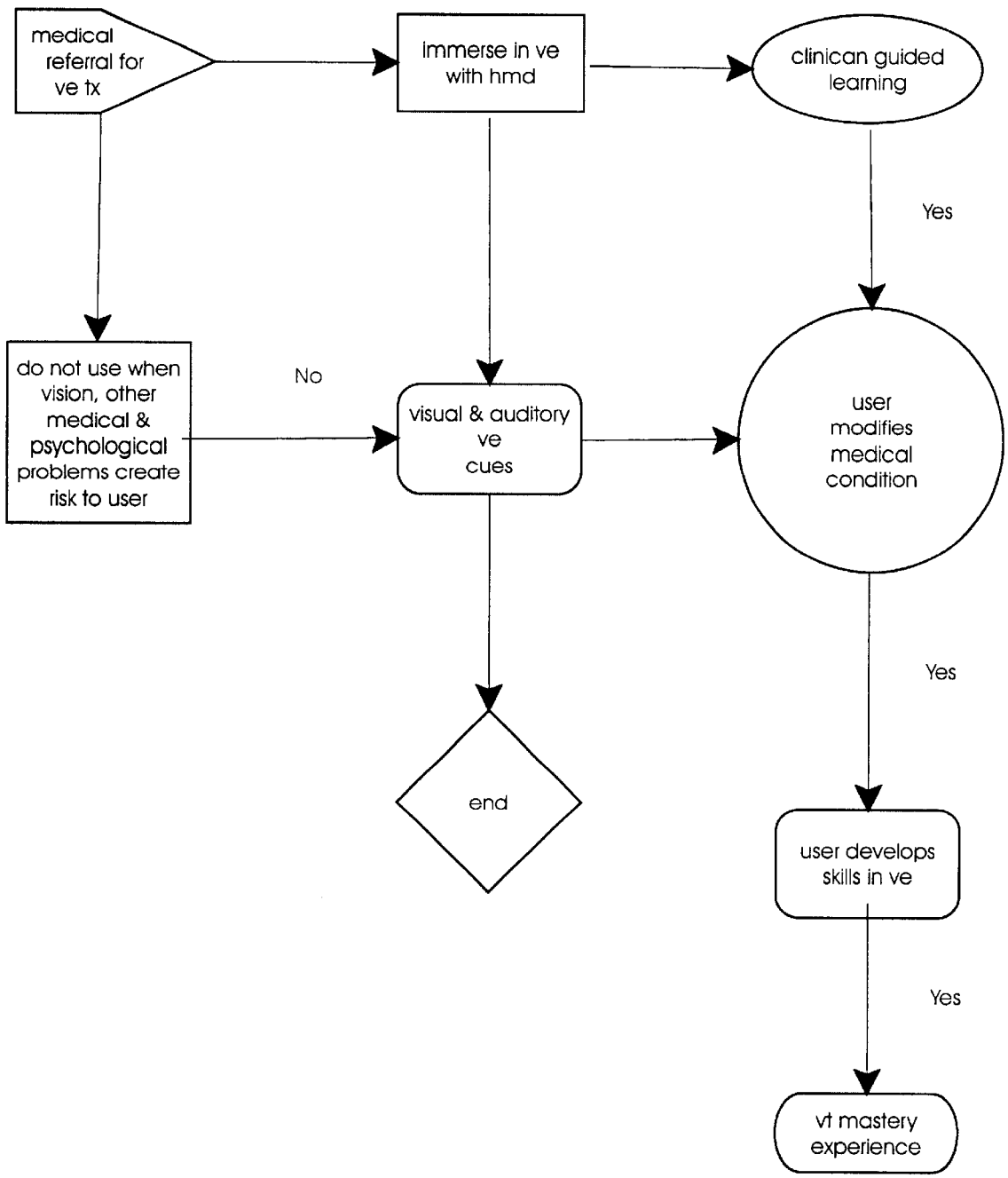
FIG. 9 is an eighth flowchart showing medical uses of a virtual environment according to the invention.

The clinician determines, according to the flow chart in FIG. 9, that exposure targeting a medical condition is the best strategy to modify neurological processes, mood, physiological conditions related to stress, healing from surgery and psychiatric hospitalization. The flowchart of FIG. 9 is similar to that of FIGS. 4 to 8 and is also self-explanatory; it outlines the therapeutic steps described below. The user is immersed in a virtual environment depicting exercise of neck, upper and lower body limbs and muscles. The purpose of this exposure is to assist the patient in developing visual imagery associated with self-efficacy. For example, users of a virtual environment fitness step-machine may achieve confidence to alter the virtual environment with exercise. A sense of climbing can be enhanced with scenes depicting arrivals at scenic viewpoints. Verbal cues reminding the user to look at the environment, enjoy the scenes, and appreciate the moment, are avenues for making positive cognitive shifts. Exercise, pleasant sensory input, and health merge by association: sensory inputs provide immediate feedback, demonstrating that challenges can be pleasant.

Visual sensory input during immersion in the virtual environment shows promise for assessing and treating medical conditions related to vision, migraine headaches, pain, strokes and other neurological states influenced by learning and memory. Virtual Therapy may also be applied to the following medical conditions:

neurology: migraine headaches, other headaches, stroke victims, obsessive-compulsive disorder
physical therapy: recovery from injury and fitness
attention deficit disorder treatment: attention and focus rehearsal
surgery: phantom limb syndrome
brain scans: distraction from anxiety-claustrophobia
ophthalmology: assessment and treatment of eye disease Greenleaf, Burdea, and Grigore, in U.S. Pat. No. 5,429,140 (1995) describe an integrated virtual reality rehabilitation system. A force feedback glove is worn by a patient to simulate virtual deformable objects. Information from the sensing glove is transmitted to a computer where it is used to diagnose the patient's manual capability. Virtual objects may be grasped with the force feedback glove and squeezed, giving the user a sense of touch. The basic concept of rehabilitation in a virtual environment utilizing force feedback may be applied to other appendages of the human body. The sense of touch can already be used in virtual environments without the use of a force feedback glove. Current hand-held grips, such as that used in Virtual Therapy, permit the user to "pick" objects, lift, move, and drop them. Real objects may be combined with the virtual environment experience to enhance a user's sense of reality for the purpose of developing skills and self-efficacy. Virtual Therapy describes a method, based upon research, which can be used in this area to achieve cognitive, emotional, and physiological rehabilitation.

Patients show increased self-efficacy after Virtual Therapy because the method enables users to achieve cognitive, emotional, and behavioral successes during immersion is a virtual environment. Increased confidence from Virtual Therapy is hypothesized to increase a psycho-neuroimmunological (PNI) response. Maier et al. (1994) state "The immune system and brain form a bidirectional interacting set of processes each regulating the other. Psychological processes can influence this network and in turn be modulated by it. Classical conditioning can modify immune processes, stress can alter immunity, and immune products can feed back and modulate behavior." Virtual Therapy strengthens immunity by modulating behavior.

Summary, Ramifications, and Scope

The reader will thus see that I have presented a particularly simple method for treating psychological, psychiatric, medical, and self-help conditions in human patients using virtual reality technology. The method uses three-dimensional, fully interactive, sensory inputs which makes the assessment, diagnosis, and treatment procedures easy to initiate and complete. The method of Virtual Therapy is less costly and less time consuming than other forms of standard-of-care treatments. Pilot studies show that 90% of patients can effectively use one fifty-minute session, to overcome longstanding avoidance and anxiety associated with acrophobia (fear of heights).

Compared to traditional talk therapy, computer generated Virtual Therapy provides patients with rapid relief from painful emotional states and elimination of avoidance associated with acrophobia, and other psychiatric and medical conditions. Other forms of treatment require patients to imagine a desired behavior or view two-dimensional computer generated scenes while using a keyboard or mouse. These treatments are not truly interactive. They are weak and require longer periods of treatment when compared to fully interactive Virtual Therapy interventions using environments that are under the control of the user.

The method of Virtual Therapy has been surprisingly effective in the assessment, prevention, and treatment of psychiatric conditions which include acrophobia and co-existing anxiety disorders, other phobias, depression, and substance related addictions. Virtual Therapy uses performance strategies in virtual environments to influence cognitive processing, emotional arousal, and skill development. Performance accomplishments, based on personal experience where mastery of a situation or task is attained, are considered the most influential in creating a sense of competence.

Accomplishments create expectations of future success. The power of the procedure will strongly determine the strength of personal belief to achieve desired goals. Virtual Therapy is psychotherapeutic because it permits assessment, diagnosis, and treatment of cognitive, emotional, and behavioral functioning of the user during immersion in the virtual environment. Sensory stimulation is known to influence habituation and sensitization (forms of learning associated with neurons) along the visual pathway. Visual sensory input during immersion in the virtual environment shows promise for assessing and treating medical conditions related to vision, migraine headaches, pain, strokes and other neurological states influenced by learning and memory. The process provides opportunities for self-help when accompanied with literature or provider directions on effective use of the virtual therapy processes.

In addition, virtual reality centers are already located in shopping malls, vacation resorts, and urban centers. This leads to consideration of convenience and self-help applications and responses in desirable environments, The patient recognizes the importance of medications and treatment regimens in an entertaining manner. Moreover, the patient participates actively in the treatment by following instructions embedded in the virtual environment or even generating positive physiological responses due to stimuli presented in the Virtual Therapy application.

The method of the invention also provides a treatment to which the patient can resort as the need arises. The intrinsic fun of a novel, interactive virtual environment ensures higher treatment compliance for all patients, and in particular, adolescents. The self-help instructions communicated by this method can additionally be used induce patients to independently perform measurements of physical parameters associated with their psychological, psychiatric, or medical condition.

An interactive multimedia program for breast cancer patients is under study by Manning (1995). The program provides information about disease and options for treatment with the hope of reducing patient distress. Though not mentioned by Manning, the effectiveness of medical procedures may be increased with immersive virtual reality applications. Virtual Therapy proposes immersing patients in calming environments while undergoing certain medical procedures such as CRT brain scans. Confronted with limited space and cautioned not to move, patients frequently experience discomfort due to claustrophobia. Many are offered medications, an invasive intervention, to lower anxiety. Virtual Therapy offers a non-invasive option to the use medication.

Finally, physiological measures recorded during the session provide an excellent standardized measure for evaluating treatment results and improving continued treatment. In carrying out the method the virtual reality technology system can be expanded to use any number of communication devices, monitoring set-ups, and other state-of-the-art medical equipment.

Therefore, the scope of the invention should not be determined by the examples given, but also by the appended claims and their legal equivalents.

What is claimed is:

1. A method for treating a psychological, psychiatric, or medical condition in a human patient, comprising:
   (a) choosing a psychological strategy for treating said psychological, psychiatric, or medical condition;
   (b) providing an interactive virtual reality environment;
      (1) said interactive virtual reality environment comprising a technology unit arranged to display to said human patient a plurality of virtual reality environments;
      (2) said technology unit having an input for receiving feedback responses to said interactive virtual reality environment from said human patient;
      (3) said technology unit arranged to change said virtual reality environment in response to said feedback responses from said human patient;
   (c) selecting said virtual reality environment to correspond to said psychological strategy;
   (d) encoding electronic instructions for said interactive virtual reality environment;
   (e) loading said electronic into said virtual reality technology unit; and
   (f) instructing said human patient how and when to use said virtual reality technology unit so as to experience said interactive virtual reality environment and how and when to provide feedback responses to said technology unit for changing said virtual reality environment so as to treat said psychological, psychiatric, or medical condition.

2. The method of claim 1 wherein said virtual reality environment corresponding to said psychological strategy and displayed by said interactive technology unit comprises a plurality of graphical images related to said psychological, psychiatric, or medical condition of said patient, and further including evaluating said feedback responses of said human patient to determine the success of said patient, thereby causing a psychological response in said human patient which will improve said patient's psychological, psychiatric, or medical condition.

3. The method of claim 2 wherein said condition in said patient is acrophobia and said graphical images have heights and depths.

4. The method of claim 2 wherein said condition in said patient is an anxiety disorder and said graphical images are selected to produce anxiety disorder disturbances in said patient.

5. The method of claim 2 wherein said condition in said patient is a mood disorder and said graphical images are selected to produce mood disorder disturbances in said patient.

6. The method of claim 2 wherein said condition in said patient is a substance-related disorder and said graphical images are selected to produce substance-related disorder disturbances in said patient.

7. The method of caim 2 wherein said condition in said patient is one that causes behavior which is destructive to said patient and said graphical images are selected to stimulate said destructive behavior in said patient.

8. The method of claim 7 wherein said destructive behavior in said patient is adolescent substance abuse.

9. The method of claim 2 wherein said condition in said patient is one that can be alleviated by an action taken by said patient, known as a self-help strategy, and said graphical images are selected to produce said self-help strategy.

10. The method of claim 1 wherein said virtual reality environment comprises a graphical representation of a situation which stimulates said psychological, psychiatric, or medical condition of said patient, and said changing said virtual reality environment is determined by responses of said human patient to said graphical representation of said situation.

11. The method of claim 1 wherein said virtual reality environment comprises a plurality of graphical images which simulate said psychological, psychiatric, or medical condition of said patient.

12. The method of claim 1 wherein said condition in said patient comprises a phobia.

13. The method of claim 1 wherein said condition in said patient comprises an anxiety disorder selected from the class consisting of a simple phobia, agoraphobia, a social phobia, an obsessive-compulsive disorder, a panic disorder, a post-traumatic stress disorder, an acute stress disorder, and a generalized anxiety disorder.

14. The method of claim 1 wherein said condition in said patient comprises a mood disorder.

15. The method of claim 14 wherein said mood disorder is learned helplessness depression.

16. The method of claim 1 wherein said condition comprises a substance-abuse disorder.

17. The method of claim 16 wherein said substance-abuse disorder is selected from the class consisting of an alcohol use and induced disorder, an amphetamine-use and induced disorder, a cannabis-use and induced disorder, a cocaine-use and induced disorder, a hallucinogen-use and induced disorder, an inhalant-use and induced disorder, a nicotine-use and induced disorder, an opioid-use and induced disorder, a sedative, hypnotic-, or anxiolytic-use and induced disorder, and a polysubstance-use and induced disorder.

18. The method of claim 1 wherein said medical condition is selected from the class consisting of a headache, a migraine headache, an obsessive-compulsive disorder, a stroke disorder, a condition requiring physical therapy, an attention deficit disorder, a surgical recovery disorder, a hospitalization recovery disorder, an visual disorder, and an irritable bowel syndrome.

19. A method of treating a psychological, psychiatric, or medical condition in a human patient comprising:
   (a) providing a plurality of sets of instructions or steps for treating said psychological, psychiatric, or medical condition;
   (b) choosing one of said sets of instructions or steps which is appropriate for treating said psychological, psychiatric, or medical condition of said human patient;
   (c) providing a virtual reality technology unit arranged to provide an interactive virtual reality environment;
      (1) said virtual reality reality technology unit being equipped with a display means;
      (2) said virtual reality technology unit also being equipped with an input means for receiving responses to said interactive virtual reality environment from said human patient;
   (d) providing a set of encoded electronic instructions for said virtual reality environment;
   (e) embedding said one set of instructions or steps in said encoded set of electronic instructions for said interactive virtual reality environment;
   (f) loading said set of electronic instructions into said virtual reality technology unit for displaying said interactive virtual reality environment; and
   (g) instructing said human patient how and when to use said virtual reality technology unit to display said interactive virtual reality environment and how to provide responses to said virtual reality environment.

20. The method of claim 19 wherein said set of instructions or steps is communicated to said patient in said interactive virtual reality environment by a graphical representation on said display means for treating said psychological, psychiatric, or medical condition, and further including evaluating said responses of said human patient to said graphical representation on said display means to define the success of said human patient to said virtual reality environment.

21. The method of claim 19, further including:
   (a) connecting to said human patient a monitoring means for measuring a physical parameter of said patient's medical condition;
   (b) encoding a second set of electronic instructions for operating said monitoring means, said second set of electronic instructions being compatible with said first set of electronic instructions; and
   (c) merging said second set of electronic instructions with said first set of electronic instructions.

22. The method of claim 19 wherein said set of instructions or steps is communicated to said patient in said interactive virtual reality environment by graphics representative of said psychological, psychiatric, or medical condition, and further including instructing said human patient about how and when to use said monitoring means while interacting with said virtual reality environment.

23. A method for treating a psychological, psychiatric, or medical condition in a human patient comprising:
   (a) providing a plurality of sets of counseling directions for treating said psychological, psychiatric, or medical condition;
   (b) choosing one of said sets of counseling directions for treating said psychological, psychiatric, or medical condition of said human patient;
   (c) providing a virtual reality technology unit arranged to provide an interactive virtual reality environment;
      (1) said virtual reality technology unit being equipped with a display means;
      (2) said virtual reality technology unit also being equipped with an input means for receiving responses to said interactive virtual reality environment from said human patient;
   (d) providing a set of encoded electronic instructions for said virtual reality environment;
   (e) embedding said one set of counseling directions in said set of encoded electronic instructions for said interactive virtual reality environment;
   (f) loading said set of electronic instructions into said virtual reality technology unit for displaying said interactive virtual reality environment; and
   (g) instructing said human patient how and when to use said virtual reality technology unit to display said interactive virtual reality environment and how to provide responses to said virtual reality environment.

24. The method of claim 23 wherein said one of said sets of counseling directions is communicated to said patient in said interactive virtual reality environment by a graphical representation on said display means for treating said psychological, psychiatric, or medical condition, and evaluating said responses of said human patient to said graphical representation on said display means to define the success of said human patient to said virtual reality environment.

25. The method of claim 24 wherein said psychological, psychiatric, or medical condition is selected from the class consisting of a phobia, an anxiety disorder, a panic disorder, a mood disorder, depression, a substance-abuse disorder, and an occupational problem.

26. A method of evaluating a psychological, psychiatric, or medical condition in a human patient, comprising:
   (a) providing a virtual reality technology unit;
   (b) said virtual reality technology unit being equipped with the following:
      (1) a display means for displaying a virtual reality environment;

(2) an input means for receiving responses to said virtual reality environment from said human patient; and (3) a scoring means for quantitatively analyzing said psychological, psychiatric, or medical condition of said patient;

(c) providing a set of encoded electronic instructions for causing said virtual reality environment to provide, on said display means, graphical representations of an environment which affects said psychological, psychiatric, or medical condition of said human patient;

(d) delivering said electronic instructions to said virtual reality environment; and (e) instructing said human patient how and when to use said virtual reality technology unit to interact with said virtual reality environment by providing responses to said graphical representations.

27. The method of claim 26 wherein said scoring procedure comprises means for recording said responses of said human patient, assigning values to said responses, and performing a computation on said assigned values to obtain a final score, and further comprising using said final score as a quantitative measure of said medical condition.

28. The method of claim 27 wherein said interactive virtual reality environment comprises a graphical environment representative of said psychological, psychiatric, or medical condition, and said responses of said human patient to said graphical representations are evaluated to define the success of said human patient to said virtual reality environment.

29. The method of claim 28 wherein said psychological, psychiatric, or medical condition is selected from the class consisting of a phobia, an anxiety disorder, a panic disorder, a mood disorder, depression, a substance-abuse disorder, and an occupational problem.

30. The method of claim 26 wherein said virtual reality environment comprises a graphical representation of a situation which stimulates said psychological, psychiatric, or medical condition of said patient, said graphical representation of a situation is predetermined by a healthcare professional, and said responses of said human patient are used to determine the success of said human patient to said graphical representation.

31. The method of claim of 30, further including evaluating said responses of said human patient to provide a final score to indicate the success of said human patient.

* * * * *

UNITED STATES PATENT AND TRADEMARK OFFICE
CERTIFICATE OF CORRECTION

PATENT NO. : 6,425,764 B1 Page 1 of 1
APPLICATION NO. : 08/989778
DATED : July 30, 2002
INVENTOR(S) : Ralph Lamson It is certified that error appears in the above-identified patent and that said Letters Patent is hereby corrected as shown below:

Col. 28, line 11:
Claim 1, clause (e), after "electronic" insert --instructions--.

Signed and Sealed this

Nineteenth Day of December, 2006

JON W. DUDAS
*Director of the United States Patent and Trademark Office*